(12) United States Patent
Kobayashi et al.

(10) Patent No.: US 8,168,053 B2
(45) Date of Patent: May 1, 2012

(54) GAS SENSING MEMBER USED FOR GAS SENSOR AND METHOD OF MANUFACTURING THE MEMBER

(75) Inventors: Kiyomi Kobayashi, Kuwana (JP); Makoto Nakae, Nagoya (JP); Toshikazu Hirose, Anjo (JP)

(73) Assignee: Denso Corporation, Kariya (JP)

( * ) Notice: Subject to any disclaimer, the term of this patent is extended or adjusted under 35 U.S.C. 154(b) by 1127 days.

(21) Appl. No.: 11/652,471

(22) Filed: Jan. 12, 2007

(65) Prior Publication Data
US 2007/0170057 A1    Jul. 26, 2007

(30) Foreign Application Priority Data

| Jan. 23, 2006 | (JP) | 2006-013986 |
| Jan. 23, 2006 | (JP) | 2006-013987 |
| Sep. 1, 2006 | (JP) | 2006-237330 |
| Sep. 26, 2006 | (JP) | 2006-259971 |

(51) Int. Cl.
*G01N 27/419* (2006.01)

(52) U.S. Cl. ........ 204/429; 204/428; 204/430; 204/424; 204/425; 204/426; 73/23.31; 73/23.32

(58) Field of Classification Search .......... 204/424–429; 205/783.5–785, 781; 73/23.31–23.32
See application file for complete search history.

(56) References Cited

U.S. PATENT DOCUMENTS

| 4,650,560 A | 3/1987 | Ueno |
| 5,160,598 A | 11/1992 | Sawada et al. |
| 5,460,711 A | 10/1995 | Riegel et al. |
| 5,538,612 A * | 7/1996 | Kojima et al. ............. 204/429 |
| 5,593,558 A * | 1/1997 | Sugino et al. ............. 204/429 |
| 6,156,176 A * | 12/2000 | Sugiyama et al. ........... 204/425 |
| 6,210,552 B1 | 4/2001 | Mizutani et al. |
| 6,645,360 B1 | 11/2003 | Eisele et al. |

(Continued)

FOREIGN PATENT DOCUMENTS

CN    86 1 00466    7/1986

(Continued)

OTHER PUBLICATIONS

Chinese Office Action dated Jun. 9, 2009, issued in corresponding Chinese Application No. 2007100040460, with English translation.

(Continued)

*Primary Examiner* — Keith Hendricks
*Assistant Examiner* — Bach Dinh
(74) *Attorney, Agent, or Firm* — Nixon & Vanderhye PC

(57) ABSTRACT

A gas sensing member has a unit structure and a porous protective layer disposed on the unit structure. The unit structure has a solid electrolyte body, a gas measurement electrode disposed on a surface of the body and exposed to a measured gas entering at a gas inlet, a reference gas electrode disposed on another surface of the body and exposed to a reference gas, and a heater disposed close to the body. The heater has a heater substrate and heating elements disposed in the heater substrate. The heating elements heat the body. The heater substrate has side corner areas placed on side corners of the unit structure and being adjacent to the heating elements. The protective layer is disposed on the gas inlet such that the side corner areas are not covered with the protective layer and are directly exposed to the measured gas.

19 Claims, 25 Drawing Sheets

U.S. PATENT DOCUMENTS

| | | | |
|---|---|---|---|
| 6,805,830 B1 | 10/2004 | Graser et al. | |
| 2002/0008025 A1* | 1/2002 | Fujii et al. | 204/429 |
| 2002/0060152 A1* | 5/2002 | Hotta et al. | 204/429 |
| 2003/0159928 A1* | 8/2003 | Kojima et al. | 204/408 |
| 2003/0188969 A1* | 10/2003 | Imamura et al. | 204/424 |
| 2004/0007462 A1* | 1/2004 | Hotta et al. | 204/429 |
| 2005/0274615 A1* | 12/2005 | Naito et al. | 204/424 |
| 2005/0284759 A1 | 12/2005 | Kawase et al. | |
| 2007/0007136 A1* | 1/2007 | Awano et al. | 204/424 |

FOREIGN PATENT DOCUMENTS

| | | |
|---|---|---|
| EP | 0 203 351 | 8/1990 |
| JP | 62-050658 | 3/1987 |
| JP | 02-212759 | 8/1990 |
| JP | 06-229982 | 8/1994 |
| JP | 11-160273 | 6/1999 |
| JP | 2000-511644 | 9/2000 |
| JP | 2001-281210 | 10/2001 |
| JP | 2002-139468 | 5/2002 |
| JP | 2003-502664 | 1/2003 |
| JP | 2003-322632 | 11/2003 |
| JP | 2004-271515 | 9/2004 |
| JP | 2006-010583 | 1/2006 |

OTHER PUBLICATIONS

Chinese Office Action dated May 8, 2009, issued in corresponding Chinese Application No. 2007100040460, with English translation.

Japanese Office Action dated Mar. 15, 2011, issued in counterpart Japanese Application No. 2006-259971, with English translation.

Japanese Office Action dated Mar. 22, 2011, issued in counterpart Japanese Application No. 2006-237330, with English translation.

* cited by examiner

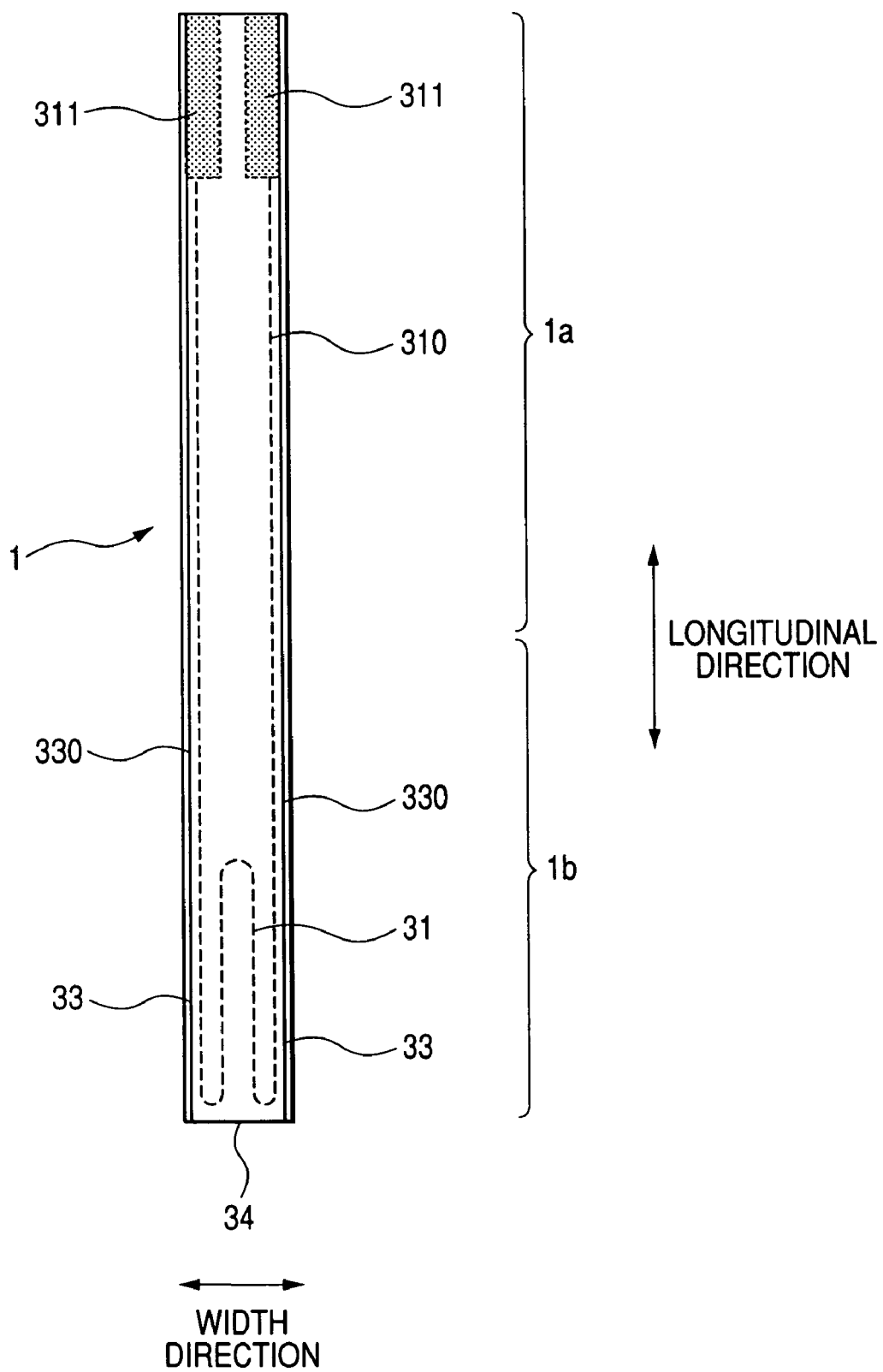

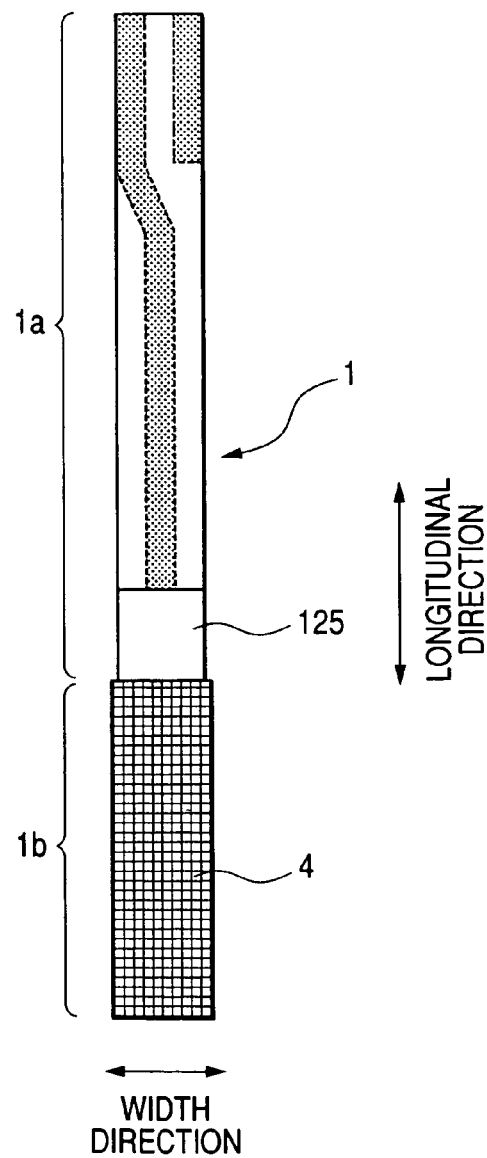
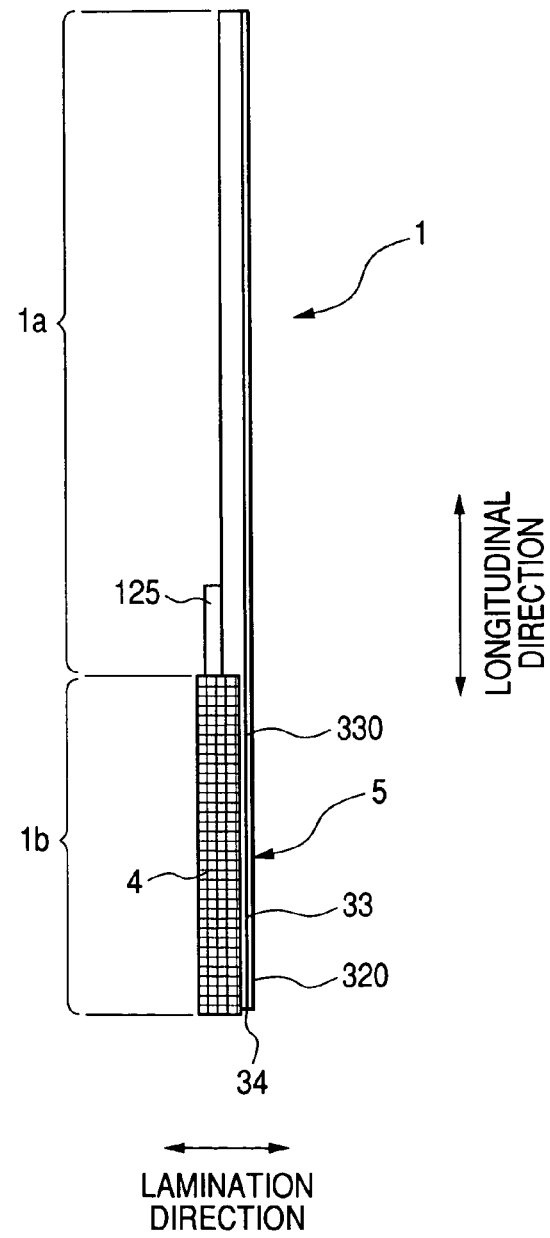

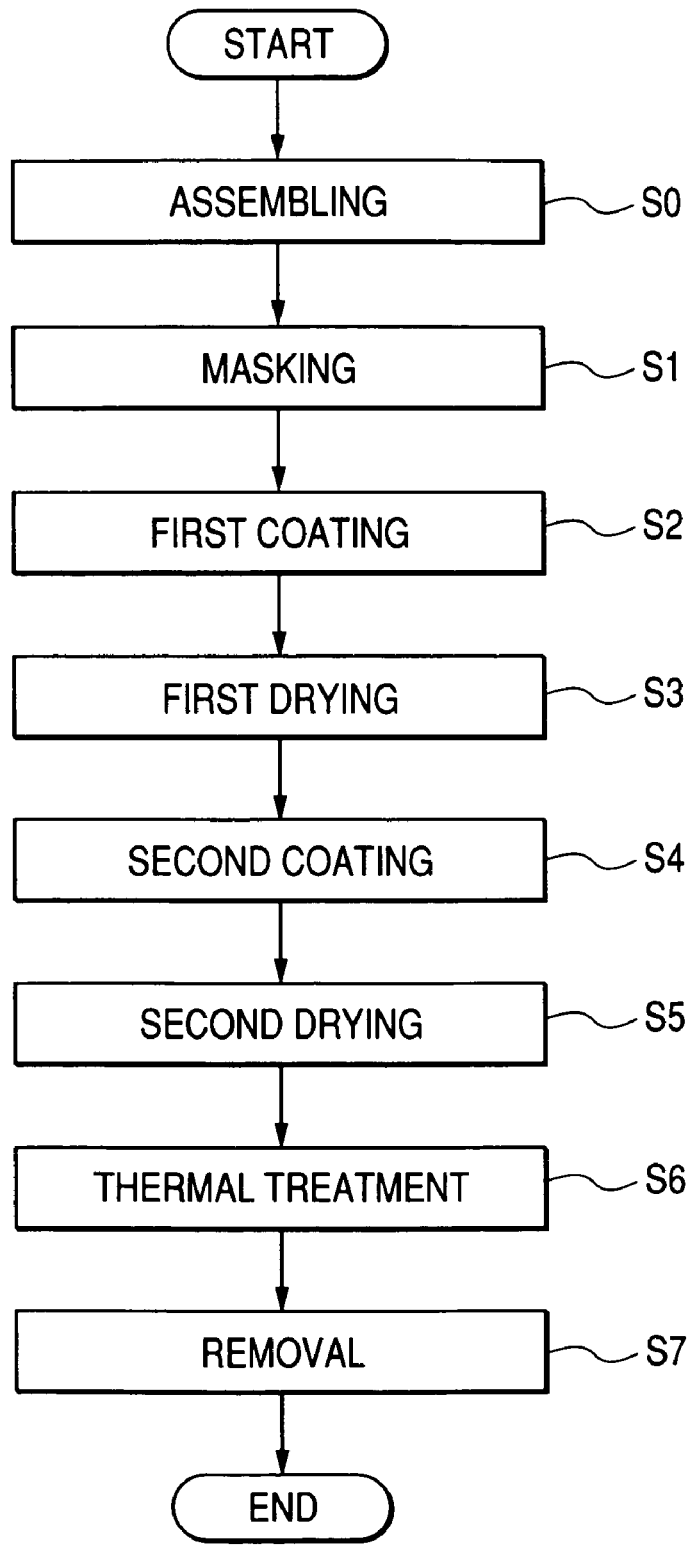

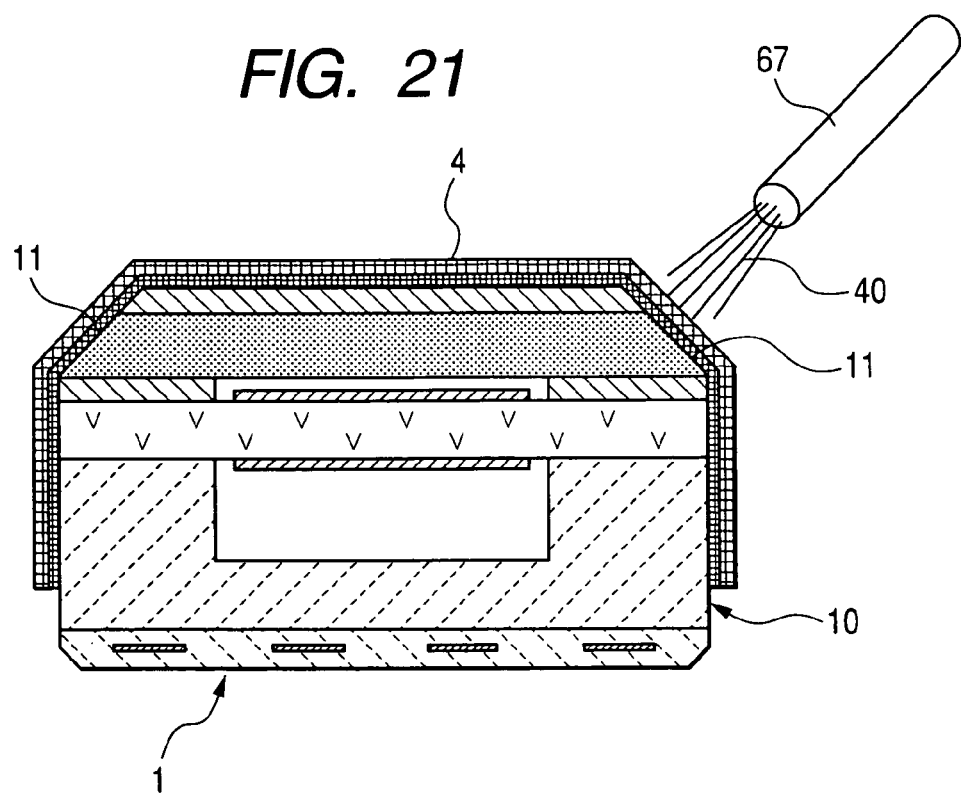
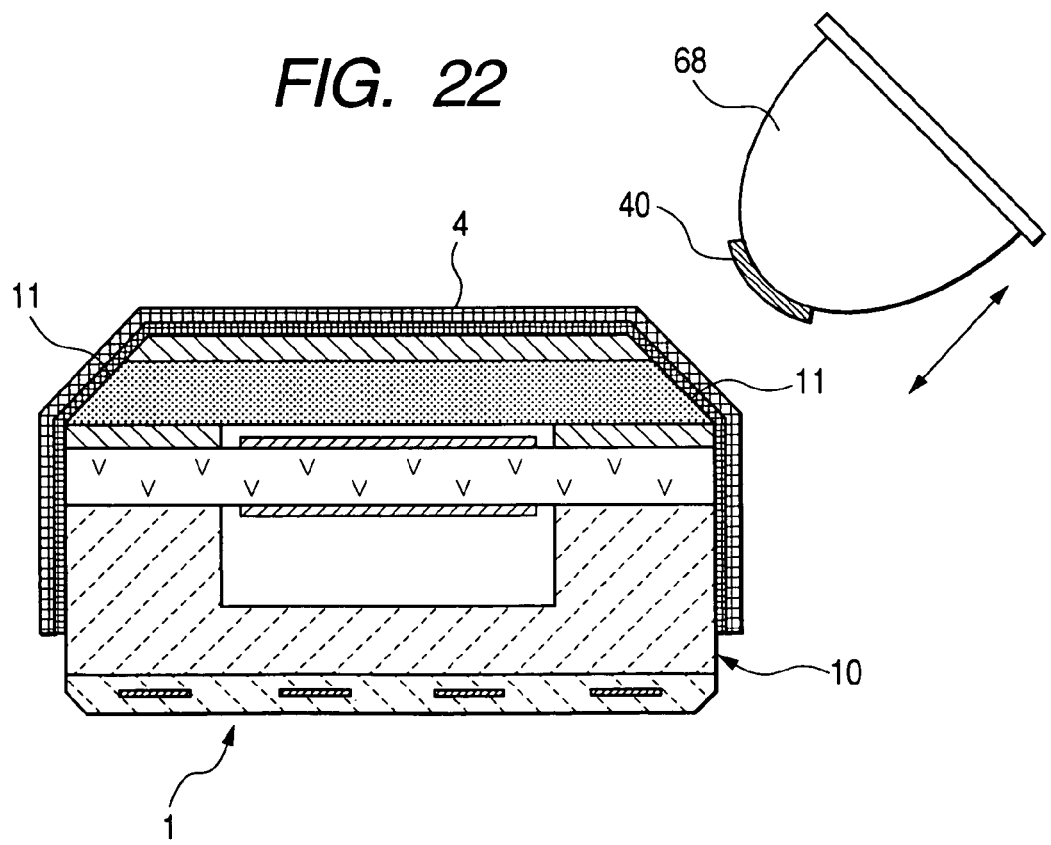

GAS SENSING MEMBER USED FOR GAS SENSOR AND METHOD OF MANUFACTURING THE MEMBER

CROSS-REFERENCE TO RELATED APPLICATION

This application is based upon and claims the benefit of priority of the prior Japanese Patent Application 2006-013986 filed on Jan. 23, 2006, the prior Japanese Patent Application 2006-013987 filed on Jan. 23, 2006, the prior Japanese Patent Application 2006-237330 filed on Sep. 1, 2006, and the prior Japanese Patent Application 2006-259971 filed on Sep. 26, 2006 so that the contents of which are incorporated herein by reference.

BACKGROUND OF THE INVENTION

1. Field of the Invention

The present invention relates to a gas sensing member which is used for a gas sensor disposed in an exhaust system of an internal combustion engine of a vehicle and detects a concentration of a specific component included in a measured gas output from the engine, and also relates to a method of manufacturing the gas sensing member.

2. Description of Related Art

A gas sensor with a gas sensing member is disposed in an exhaust system of an internal combustion engine of a vehicle. The gas sensing member is formed in a rectangular parallelepiped. The member has a plate-shaped solid electrolyte body having upper and lower surfaces opposite to each other along a lamination direction of the member, a gas measurement electrode disposed on the upper surface of the electrolyte body and exposed to a measured gas, a reference gas electrode disposed on the lower surface of the electrolyte body and exposed to a reference gas, and a heater disposed under the lower surface of the electrolyte body to heat the body to an activity temperature of the body. The electrolyte body has a high electric conductivity for oxygen ions.

In this sensing member, when the operation of the engine is started, the heater heats the electrolyte body to an activate temperature of the body to activate the body. When an exhaust gas output from the engine flows through the exhaust system, the gas measurement electrode is exposed to the exhaust gas, and oxygen ions obtained by decomposing the exhaust gas or the reference gas pass through the electrolyte body from one of the electrodes to the other electrode. Therefore, an electric potential difference is generated between the electrodes. Then, a concentration of a specific component (e.g., $O_2$ or NOx) included in the exhaust gas is detected from the electric potential difference.

The sensing member further has a gas inlet through which the exhaust gas is entered into a gas chamber. The gas measurement electrode is exposed to the exhaust gas in the gas chamber. The exhaust gas has poison which adversely influences the gas measurement electrode. To protect this electrode from the poisons, the whole outer surface of the sensing member is covered with a porous protective layer so as to cover the gas inlet with the protective layer. The exhaust gas is transmittable through the protective layer. When the exhaust gas passing through the gas inlet is entered into the gas chamber, the poisons of the exhaust gas are caught or trapped by the protective layer disposed on the gas inlet. Therefore, the measures gas electrode is exposed to the exhaust gas substantially not having poisons, so that the electrode can be protected from the poisons of the exhaust gas.

To form the protective layer on the sensing member, a distal portion of the sensing member to be exposed to the exhaust gas is dipped into a slurry solution wherein ceramic particles are mixed with solvent, and the slurry solution adhering to the sensing member is dried. Therefore, a layer of ceramic particles is attached to the whole surface of the distal portion of the sensing member. A proximal portion of the member is inserted into a holder of a gas sensor, so that the proximal portion is not exposed to the exhaust gas. The proximal and distal portions of the member are aligned with each other along a longitudinal direction perpendicular to the lamination direction.

Further, drops of water are produced in the engine due to combustion of fuel and are inevitably included in the exhaust gas as moisture. During the detection in the gas sensing member, the drops of water fly with the exhaust gas and are attached on the outer surface of the porous protective layer. The porous layer has a high water holding property, so that the drops of water attached to the protective layer easily adhere to and penetrate into the protective layer. Therefore, the temperature at a portion of the protective layer receiving the water is locally lowered. Particularly, when the drops of water are attached to a portion of the protective layer placed on the heater and reach the outer surface of the heater which is maintained at a high temperature, the temperature of the surface of the heater is rapidly lowered, and a large difference in temperature is generated between a water receiving area and an area surrounding the water receiving area on the surface of the heater. Therefore, thermal stress is generated in the heater, and there is a probability that the heater will be cracked or broken due to this thermal stress. For example, heating elements disposed in the heater are occasionally broken or disconnected from a power supply line.

More specifically, the heater is formed in a thin plate shape and is placed at the bottom of the sensing member. The heater has a heater substrate and a plurality of heating elements buried in the heater substrate. The heating elements are aligned with one another in the distal portion of the member along a width direction perpendicular to the lamination and longitudinal directions. Each heating element extends along the longitudinal direction. The heater substrate has side corner portions on both sides in the width direction. The side corner portions are placed at bottom side corners of the sensing member. When drops of water are attached on a particular area of the protective layer just placed on one side corner portion of the heater substrate, thermal stress is caused on the side corner portion of the heater substrate. Because the side corner portion of the heater substrate is placed at a corner of the sensing member, the thermal stress is easily concentrated on a narrow area. Therefore, there is a high probability that the heater is cracked or broken at its side corner portion.

For example, Published Japanese Patent First Publication No. 2003-322632 discloses a gas sensing member. In this Publication, to prevent breakage of the sensing member caused by drops of water attached on the outer surface of the sensing member, the whole surface of the distal portion of the member is covered with a porous protective layer. However, because the porous layer has a high water holding property, drops of water attached on the outer surface of the protective layer easily penetrate into the protective layer and reach the outer surface of the sensing member to lower the temperature of the sensing member. Particularly, when drops of water are attached on a particular surface area of the protective layer placed on a side corner portion of a heater, a thermal stress is concentrated in the side corner portion, and the heater is easily broken or cracked. Therefore, the protective layer disposed on the side corner area of the heater does not protect the heater, but rather heighten a probability of the breakage of the heater.

To prevent drops of water attached on the surface of the protective layer from reaching the surface of the sensing member, there is an idea that a protective layer disposed on the sensing member is thickened. In this case, the drops of water attached on the surface of the protective layer are dispersed in the protective layer along directions parallel to the surface of the protective layer. Therefore, the drops of water do not reach the sensing member, and breakages and cracks of the sensing member can be prevented. However, the thickened protective layer increases a thermal capacity of the sensing member. In this case, when the operation of the engine is started, it takes a long time to heat the sensing member, and the electrolyte body of the sensing member cannot rapidly reach its activity temperature. Therefore, when the operation of the engine is started, it becomes difficult to accurately detect a concentration of a specific component included in the exhaust gas, and it is very likely that fuel will not completely combust in the engine.

SUMMARY OF THE INVENTION

An object of the present invention is to provide, with due consideration to the drawbacks of the conventional gas sensing member, a gas sensing member wherein cracks or breakages caused by water attached to the member are suppressed while a heat capacity of the member is reduced.

Further, the object of the present invention is to provide a method of manufacturing the gas sensing member.

According to a first aspect of this invention, the object is achieved by the provision of a gas sensing member having a unit structure, and a porous protective layer disposed on the unit structure. The unit structure has a solid electrolyte body having a high electric conductivity for oxygen ions and having both surfaces opposite to each other along a first direction, a gas measurement electrode disposed on one surface of the solid electrolyte body, a reference gas electrode disposed on the other surface of the solid electrolyte body, and a heater disposed on or close to the solid electrolyte body so as to face one of the surfaces of the solid electrolyte body. The gas measurement electrode is exposed to a measured gas entering at a gas inlet of the unit structure. The reference gas electrode is exposed to a reference gas. The heater has a heater substrate and a heating element disposed in or on the heater substrate. The heating element heats the solid electrolyte body. The heater substrate has a side corner area which is placed on a side corner surface of the unit structure in a second direction substantially perpendicular to the first direction and extends along a third direction substantially perpendicular to the first and second directions so as to be adjacent to the heating element along the second direction. The porous protective layer is disposed at least on the gas inlet so as to indirectly expose the gas measurement electrode to the measured gas transmitted through the porous protective layer such that at least a portion of the side corner area of the heater substrate is allowed to be directly exposed to the measured gas.

With this arrangement of the gas sensing member, assuming that the side corner area is covered with the porous protective layer, water attached on the porous protective layer reaches the side corner area due to a water holding property of the porous protective layer. In this case, the temperature of the side corner area heated by the heating element is locally lowered, so that a thermal stress is easily generated in the side corner area. This thermal stress is easily concentrated on a narrow area in the side corner area. Therefore, there is a high probability that the gas sensing member is cracked or broken due to the thermal stress.

However, in the present invention, at least a portion of the side corner area of the heater substrate is directly exposed to the measured gas. When drops of water are attached on the portion of the side corner area heated by the heating element, the drops of water are immediately detached from the surface of the heater substrate due to the Leidenfrost phenomenon as if the heater substrate repels the drops of water, and the heater substrate heated by the heating element prevents the drops of water from being spread out on the side corner area.

Accordingly, a temperature drop of the side corner area is considerably lowered, so that cracks and breakages of the gas sensing member can be considerably suppressed. Further, because the porous protective layer is not disposed on the whole surface of the unit structure, a heat capacity of the gas sensing member can be reduced. Moreover, because the gas measurement electrode is exposed to the measured gas transmitted through the porous protective layer, the gas measurement electrode can be protected from poisons of the measured gas.

According to a second aspect of this invention, the object is achieved by the provision of a gas sensing member having a unit structure, and a porous protective layer disposed on the unit structure. The unit structure has the solid electrolyte body, the gas measurement electrode, the reference gas electrode, and a heater disposed on or close to the solid electrolyte body so as to face one of the surfaces of the solid electrolyte body. The heater heats the solid electrolyte body. The porous protective layer is disposed at least on the gas inlet such that the gas measurement electrode is allowed to be indirectly exposed to the measured gas transmitted through the porous protective layers and such that at least a part of a particular surface of the unit structure placed opposite to the heater with respect to the solid electrolyte body is allowed to be directly exposed to the measured gas.

With this arrangement of the gas sensing member, a part of the particular surface of the unit structure is directly exposed to the measured gas. Accordingly, even when drops of water are attached on the part of the particular surface, cracks and breakages of the gas sensing member can be considerably suppressed due to the Leidenfrost phenomenon. Further, because the porous protective layer is not disposed on the whole surface of the unit structure, a heat capacity of the gas sensing member can be reduced.

According to a third aspect of this invention, the object is achieved by the provision of a method of manufacturing a gas sensing member, having the steps of assembling, into a unit structure, the solid electrolyte body, the gas measurement electrode, the reference gas electrode, and the heater having the side corner area of the heater substrate placed on a side corner surface of the unit structure, and forming a porous protective layer on the unit structure. The step of forming the porous protective layer has forming a mask layer made of an organic material on at least a portion of the side corner area of the heater substrate of the heater, attaching a protective layer forming material on a surface of the unit structure such that at least the gas inlet and the mask layer are covered with the protective layer forming material, performing a thermal treatment for the protective layer forming material to change the protective layer forming material to the porous protective layer such that the gas measurement electrode is allowed to be exposed to the measured gas transmitted through the porous protective layer, and removing the mask layer and the porous protective layer attached on the mask layer from the unit structure such that at least the portion of the side corner area is allowed to be directly exposed to the measured gas.

In this method, at least a portion of the side corner area is directly exposed to the measured gas, and the gas inlet is covered with the porous protective layer. Accordingly, the gas sensing member in the first aspect can be reliably manufactured. Further, because the mask layer and the porous protective layer attached on the mask layer are removed from the unit structure only at one step, the gas sensing member can be efficiently manufactured.

According to a fourth aspect of this invention, the object is achieved by the provision of a method of manufacturing a gas sensing member, having the steps of assembling the unit structure, and forming a porous protective layer on the unit structure. The step of forming the porous protective layer has attaching a protective layer forming material at least on the gas inlet of the unit structure such that at least a portion of the side corner area of the heater substrate of the heater is not covered with the protective layer forming material, and performing a thermal treatment for the protective layer forming material to change the protective layer forming material attached on the gas inlet to the porous protective layer such that the gas measurement electrode is allowed to be indirectly exposed to the measured gas transmitted through the porous protective layer, and such that at least the portion of the side corner area is allowed to be directly exposed to the measured gas.

In this method, at least a portion of the side corner area is directly exposed to the measured gas, and the gas inlet is covered with the porous protective layer. Accordingly, the gas sensing member in the first aspect can be reliably manufactured.

According to a fifth aspect of this invention, the object is achieved by the provision of a method of manufacturing a gas sensing member, having the steps of assembling the unit structure, and forming a porous protective layer on the unit structure. The step of forming the porous protective layer has attaching the porous protective layer on both the gas inlet of the unit structure and at least a portion of the side corner area of the heater substrate of the heater, removing a portion of the porous protective layer, which is disposed at least on the portion of the side corner area of the heater substrate, such that at least the portion of the side corner area of the heater substrate is allowed to be directly exposed to the measured gas and such that the gas measurement electrode is allowed to be indirectly exposed to the measured gas transmitted through the porous protective layer, and performing a thermal treatment for the porous protective layer.

In this method, at least a portion of the side corner area is directly exposed to the measured gas, and the gas inlet is covered with the porous protective layer. Accordingly, the gas sensing member in the first aspect can be reliably manufactured.

According to a sixth aspect of this invention, the object is achieved by the provision of a method of manufacturing a gas sensing member, having the steps of assembling, into a unit structure, the solid electrolyte body, the gas measurement electrode, the reference gas electrode and a heater disposed on or close to the solid electrolyte body so as to face one of the surfaces of the solid electrolyte body and heating the solid electrolyte body, and forming a porous protective layer on the unit structure. The step of forming the porous protective layer has forming a mask layer made of an organic material at least on a part of a particular surface of the unit structure placed opposite to the heater with respect to the solid electrolyte body, attaching a protective layer forming material on the unit structure such that at least both the gas inlet and the mask layer are covered with the protective layer forming material, performing a thermal treatment for the protective layer forming material to change the protective layer forming material to the porous protective layer such that the gas measurement electrode is allowed to be indirectly exposed to the measured gas transmitted through the porous protective layer, and removing the mask layer and the porous protective layer attached on the mask layer from the unit structure such that at least the part of the particular surface of the unit structure placed opposite to the heater with respect to the solid electrolyte body is allowed to be directly exposed to the measured gas.

In this method, the gas inlet is covered with the porous protective layer, and at least a part of the particular surface of the unit structure placed opposite to the heater with respect to the solid electrolyte body is not covered with the porous protective layer. Accordingly, the gas sensing member in the second aspect can be reliably manufactured. Further, because the mask layer and the porous protective layer attached on the mask layer are removed from the unit structure only at one step, the gas sensing member can be efficiently manufactured.

According to a seventh aspect of this invention, the object is achieved by the provision of a method of manufacturing a gas sensing member, having the steps of assembling the unit structure, and forming a porous protective layer on the unit structure. The step of forming the porous protective layer has attaching a protective layer forming material on at least the gas inlet of the unit structure such that at least a part of a particular surface of the unit structure placed opposite to the heater with respect to the solid electrolyte body is not covered with the protective layer forming material, and performing a thermal treatment for the protective layer forming material to change the protective layer forming material attached on the gas inlet to the porous protective layer such that the gas measurement electrode is allowed to be indirectly exposed to the measured gas transmitted through the porous protective layer and such that at least the part of the particular surface of the unit structure placed opposite to the heater with respect to the solid electrolyte body is allowed to be directly exposed to the measured gas.

In this method, the gas inlet is covered with the porous protective layer, and at least a part of the particular surface of the unit structure placed opposite to the heater with respect to the solid electrolyte body is not covered with the porous protective layer. Accordingly, the gas sensing member in the second aspect can be reliably manufactured.

According to an eighth aspect of this invention, the object is achieved by the provision of a method of manufacturing a gas sensing member, having the steps of assembling the unit structure, and forming a porous protective layer on the unit structure. The step of forming the porous protective layer has attaching the porous protective layer on both the gas inlet of the unit structure and at least a part of a particular surface of the unit structure placed opposite to the heater with respect to the solid electrolyte body, removing a portion of the porous protective layer, which is disposed at least on the part of the particular surface of the unit structure, such that at least the part of the particular surface of the unit structure is allowed to be directly exposed to the measured gas and such that the gas measurement electrode is allowed to be indirectly exposed to the measured gas transmitted through the porous protective layer, and performing a thermal treatment for the porous protective layer.

In this method, the gas inlet is covered with the porous protective layer, and at least a part of the particular surface of the unit structure placed opposite to the heater with respect to the solid electrolyte body is not covered with the porous protective layer. Accordingly, the gas sensing member in the second aspect can be reliably manufactured.

BRIEF DESCRIPTION OF THE DRAWINGS

FIG. 3 is a rear view, partly in cross section, of the gas sensing member shown in FIG. 1;

FIG. 4 is a plan view of the sensing member shown in FIG. 1;

FIG. 5 is a side view of the sensing member shown in FIG. 1;

FIG. 6 is a flow chart showing a method of manufacturing the sensing member shown in FIG. 1 to FIG. 5;

FIG. 21 is an explanatory view showing a method of attaching a protective layer forming material to a unit structure according to the fourth embodiment;

FIG. 22 is an explanatory view showing a method of attaching a protective layer forming material to a unit structure according to the fifth embodiment;

DETAILED DESCRIPTION OF THE PREFERRED EMBODIMENTS

Figure 1:
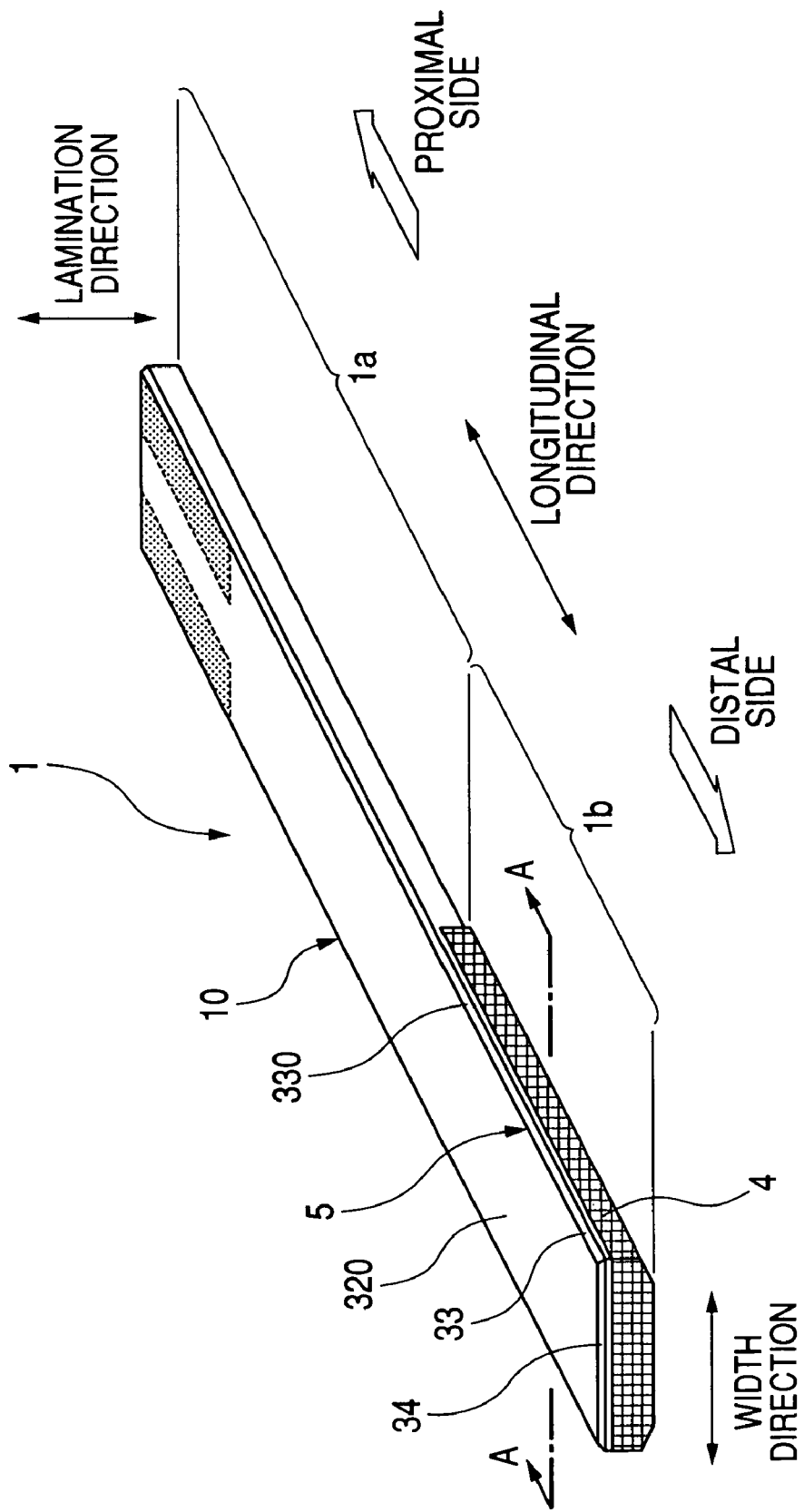
FIG. 1 is a perspective side view of a gas sensing member according to the first embodiment of the present invention.

The inventors of the present invention have conducted experiments to analyze how a gas sensing member covered with a porous protective layer is cracked or broken when receiving drops of water. As a result of analysis for these experiments, they have discovered that drops of water attached to the surface of the protective layer were immediately absorbed and dispersed into the protective layer due to a high water holding property of the protective layer so as to rapidly lower the temperature of a limited surface area of the sensing member. Therefore, they have realized that the protective layer disposed on the sensing member lowers a water resisting property of the sensing member rather than protects the sensing member. Particularly, when drops of water are attached to a specific surface area of the protective layer placed on a side corner portion of a heater, a thermal stress is caused by the attachment of the drops of water to the side corner portion of the heater and is easily concentrated on a narrow area. Therefore, there is a high probability that the heater is cracked or broken at its side corner portion.

In contrast, they have realized that the sensing member covered with no porous layer is superior in a water resisting property. More specifically, when drops of water are attached on a surface of the sensing member covered with no porous layer and heated at a high temperature, the drops of water are immediately detached from the surface of the sensing member due to the well-known Leidenfrost phenomenon as if the sensing member repels the drops of water, and the sensing member heated at a high temperature prevents the drops of water from being spread out on the surface of the sensing member. Therefore, as compared with a gas sensing member covered with a porous layer, a temperature drop in the sensing member covered with no porous layer can be considerably suppressed. As a result, even though the surface of the sensing member covered with no porous layer and heated at a high temperature is exposed to a measured gas such as an exhaust gas including drops of water, the sensing member is hardly cracked or broken due to drops of water attached on the surface of the sensing member.

Here, when drops of water come in contact with a surface of a member heated at a high temperature such as 100° C., a portion of the water being in contact with the surface is immediately vaporized, and the obtained steam placed between the surface of the sensing member and the water acts as a heat insulating layer. This phenomenon is called the Leidenfrost phenomenon.

Based on this knowledge, the inventors provide a gas sensing member having a unit structure and a porous protective layer disposed on the unit structure. The unit structure has a solid electrolyte body having a high electric conductivity for oxygen ions and having both surfaces opposite to each other along a first direction, a gas measurement electrode disposed on one surface of the electrolyte body, a reference gas electrode disposed on the other surface of the electrolyte body, and a heater disposed on or close to the electrolyte body so as to face one of the surfaces of the electrolyte body and having a heater substrate and a heating element disposed in or on the heater substrate. The heating element heats the electrolyte body. The gas measurement electrode is exposed to a measured gas entering at a gas inlet of the unit structure. The reference gas electrode is exposed to a reference gas. The heater substrate has a side corner area which is placed on a side corner surface of the unit structure in a second direction substantially perpendicular to the first direction and extends along a third direction substantially perpendicular to the first and second directions so as to be adjacent to the heating element along the second direction. The protective layer is disposed at least on the gas inlet such that the gas measurement electrode is allowed to be indirectly exposed to the measured gas transmitted through the protective layer and such that at least a portion of the side corner area of the heater substrate is allowed to be directly exposed to the measured gas.

Because a portion of the side corner area of the heater substrate is not covered with any porous layer but is directly exposed to the measured gas, a temperature drop of the side corner area of the heater substrate caused by drops of water is suppressed due to the Leidenfrost phenomenon. Accordingly, breakages and cracks of the sensing member can be considerably suppressed even when drops of water are attached on the portion of the side corner area of the heater substrate. Further, because the protective layer is not disposed on the whole surface of the sensing member, a heat capacity of the sensing member can be reduced, and the electrolyte body can be quickly heated by the heater.

Embodiments of the present invention will now be described with reference to the accompanying drawings. However, these embodiments should not be construed as limiting the present invention to structures of those embodiments, and the structure of this invention may be combined with that based on the prior art.

Embodiment 1

A gas sensing member according to this embodiment will be described with reference to FIGS. 1 to 5.

Figure 2:
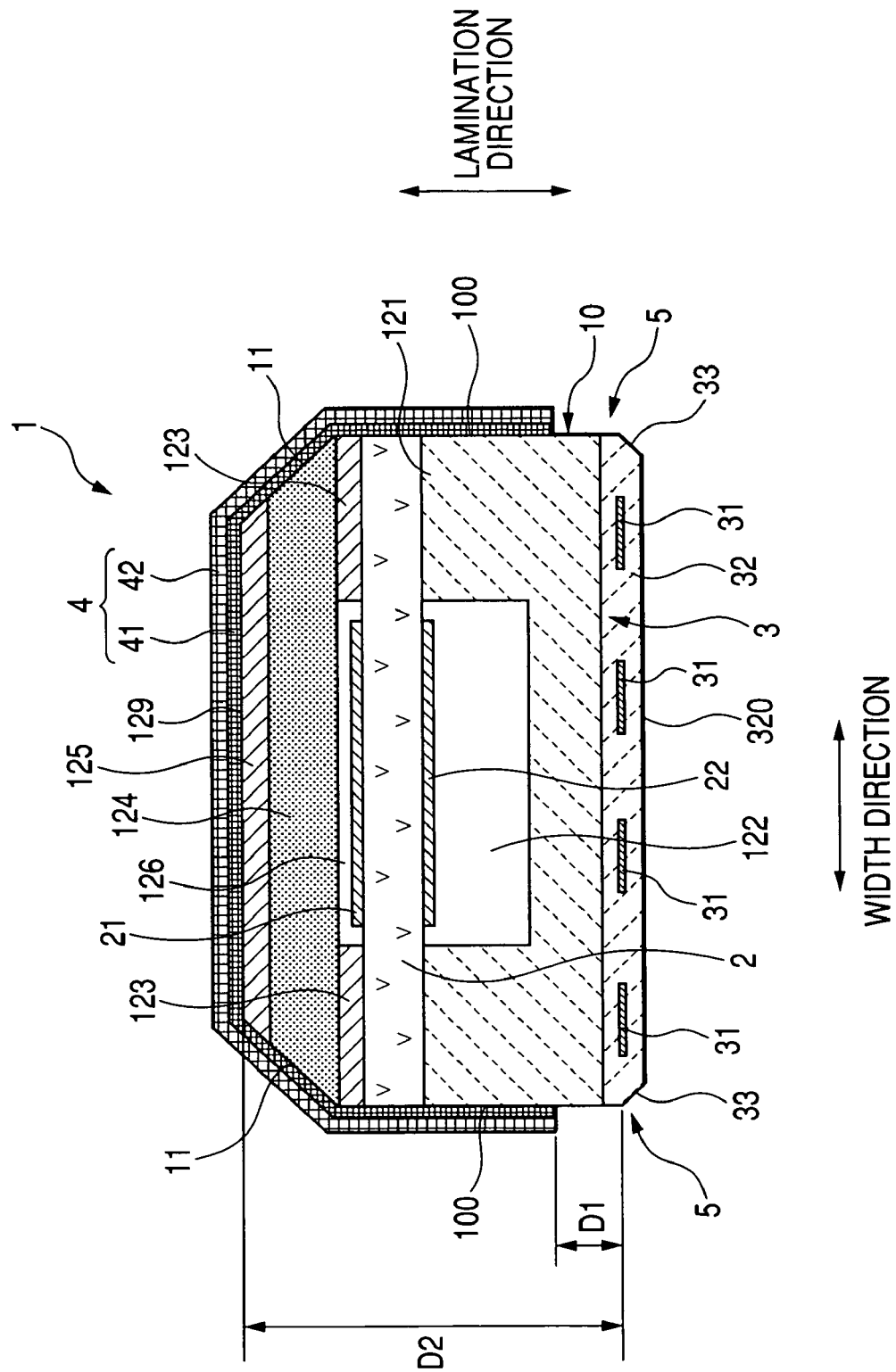
FIG. 2 is a vertical sectional view taken substantially along line A-A of FIG. 1.

FIG. 1 is a perspective side view of a gas sensing member according to the first embodiment of the present invention. FIG. 2 is a vertical sectional view taken substantially along line A-A of FIG. 1. FIG. 3 is a rear view, partly in cross section, of the sensing member shown in FIG. 1. FIG. 4 is a plan view of the sensing member shown in FIG. 1. FIG. 5 is a side view of the sensing member shown in FIG. 1.

As shown in FIG. 1, a gas sensing member 1 is formed almost in a rectangular parallelepiped shape and extends along a longitudinal direction from a proximal side to a distal side. The member 1 is partitioned into a root portion 1a placed on the proximal side and a gas sensing portion 1b placed on the distal side. The portion 1a of the sensing member 1 is inserted into an insulator (e.g., element 13 shown in FIG. 9) of a gas sensor (not shown) and is sealed with a sealing material (not shown). The gas sensor with the sensing member 1 is placed in an exhaust pipe of an internal combustion engine of a vehicle (not shown) so as to be used for an exhaust gas feedback system. The gas sensor with the sensing member 1 is, for example, used as an air-to-fuel sensor or an oxygen sensor for detecting a concentration of oxygen included in the exhaust gas, or an $NO_x$ sensor for detecting a concentration of $NO_x$ included in the exhaust gas to detect deterioration of a three-way catalyst disposed in the exhaust pipe. The sensing portion 1b of the sensing member 1 is exposed to a measured gas such as an exhaust gas output from the engine. The portion 1a of the sensing member 1 is not exposed to the measured gas. The member 1 in FIG. 1 is shown upside down to clearly illustrate a bottom surface 320 of the sensing member 1.

As shown in FIG. 2, the sensing member 1 has a unit structure 10 and a porous protective layer 4 disposed on a coating surface area of the unit structure 10. The unit structure 10 has a plate-shaped solid electrolyte body 2 having upper and lower surfaces opposite to each other along a lamination direction substantially perpendicular to the longitudinal direction, a gas measurement electrode 21 disposed on the upper surface of the electrolyte body 2, a reference gas electrode 22 disposed on the lower surface of the electrolyte body 2, and a heater 3 disposed close to the electrolyte body 2. The electrolyte body 2 is, for example, made of zirconia ($ZrO_2$) as a major material and has a high electric conductivity for oxygen ions. Oxygen ions are transmittable between the surfaces of the electrolyte body 2. The electrode 21 is exposed to a measured gas transmitted through gas inlets 11 of the unit structure 10. The electrode 22 is exposed to a reference gas. The gas inlets 11 are placed on the surface of the portion 1b of the sensing member 1. However, the gas inlets 11 may be placed on the surfaces of the portions 1a and 1b of the sensing member 1.

As shown in FIGS. 1, 2, 4 and 5, a coating surface area of the unit structure 10 is covered with the protective layer 4 so as to dispose the protective layer 4 at least on the gas inlets 11 placed on the surface of the portion 1b. The coating surface area of the unit structure 10 is not directly exposed to the atmosphere or the measured gas. The other surface of the unit structure 10 not covered with the protective layer 4 is directly exposed to the atmosphere or the measured gas and is called an uncovered surface area 5 in this specification.

As shown in FIGS. 1 and 2, the heater 3 has a heater substrate 32 and a plurality of heating elements 31 aligned one another along a width direction substantially perpendicular to the longitudinal and lamination directions. The heating elements 31 are buried in the heater substrate 32. The heater substrate 32 has a bottom surface 320 on an opposite side to the electrolyte body 2. The unit structure 10 is chamfered to remove four angular corner portions from the unit structure 10. The heater substrate 32 has two side corner areas 33, respectively, placed on two bottom chamfered surfaces of the unit structure 10. The side corner areas 33 are, respectively, placed on both sides of the bottom surface 320 in the width direction so as to be opposite to each other and be placed adjacent to the elements 31 along the width direction.

The uncovered surface area 5 includes at least a portion of the side corner areas 33 of the heater substrate 32. That is, at least a portion of the side corner areas 33 is directly exposed to the measured gas. In this embodiment, the whole side corner areas 33 are preferably covered with no protective layer so as to be directly exposed to the measured gas.

As shown in FIG. 2, the unit structure 10 of the sensing member 1 may further has a chamber forming layer 121 disposed between the electrolyte body 2 and the heater 3 so as to form a reference gas chamber 122 between the body 2 and the layer 121, a porous diffused resistor layer 124 through which the measured gas is transmittable, a spacer layer 123 disposed between the electrolyte body 2 and the layer 124 so as to form a measured gas chamber 126 between the body 2 and the layer 124, and a shielding layer 125 disposed on the layer 124. That is, the sensing member 1 is formed of a lamination of the heater 3, the layer 121, the electrolyte body 2, the spacer 123 and the layers 124 and 125 layered one another along the lamination direction. The electrode 22 faces the chamber 122 and is exposed to the reference gas filled in the chamber 22. The electrode 21 faces the chamber 126 and is exposed to the measured gas filled in the chamber 126. The layers 124 and 125 are formed at least in the sensing portion 1b of the sensing member 1. Each of the layers 121, 124 and 125 is made of alumina ($Al_2O_3$) as a major material. The layer 125 is densely formed, so that the measured gas hardly passes through the layer 125. Side portions of the layers 124 and 125 in the width direction are tapered.

The upper and side surfaces of the layer 125, the side surfaces of the layer 124 and the electrolyte body 2 and a portion of each side surface of the layer 121 form the coating surface area and are covered with the protective layer 4 so as not to be directly exposed to the measured gas flowing through the exhaust pipe. A measured gas flowing through the exhaust pipe is transmitted through the porous layer 4 disposed on the porous layer 124 and enters into the unit structure 10 at the gas inlets 11 placed on side surfaces of the porous layer 124. Then, the measured gas is transmitted through the porous layer 124 and reaches the gas chamber 126.

As shown in FIG. 3, the heater 3 may further have heater terminals 311 placed in the root portion 1a, and a heater pattern 310 connecting the terminals 311 and the heating elements 31. The heater pattern and terminals 310 and 311 are buried in the heater substrate 32. The heating elements 31 are formed by bending an end portion of the heater pattern 310 in a zigzag shape in the portion 1b. An electric current is supplied to the heating elements 31 through the terminals 311, and the heating elements 31 heat the electrolyte body 2 to an activity temperature to activate the electrolyte body 2.

The heater substrate 32 further has two second side corner areas 330 placed on the chamfered surfaces of the heater substrate 32 in the sensing portion 1b so as to extend, respectively, from the side corner areas 33. The second side corner areas 330 are adjacent to the heater pattern 310 along the width direction. In this embodiment, as shown in FIGS. 2, 4 and 5, the uncovered surface area 5 extends over the whole side corner areas 33 and 330 such that the whole side corner areas 33 and 330 are directly exposed to the atmosphere or the measured gas. However, the side corner areas 33 and 330 not covered with the protective layer 4 may be set to be equal to or larger than 60% of the side corner areas 33 and 330 placed in the gas sensing portion 1b.

As shown in FIG. 1, the heater substrate 32 further has a front corner surface 34 placed at a lower corner of the unit structure 10 in the longitudinal direction. In this embodiment, as shown in FIGS. 1 and 2, the protective layer 4 is formed on the surface of the gas sensing portion 1b except for the side corner areas 33 and 330, the front corner surface 34, the bottom surface 320 of the heater substrate 32 and parts of the side surfaces of the layer 121 adjacent to the side corner areas 33 and 330. That is, the uncovered surface area 5 extends over the side corner areas 33 and 330, the front corner surface 34, the bottom surface 320 of the heater substrate 32 and parts of the side surfaces of the layer 121 adjacent to the side corner areas 33 and 330.

More specifically, as shown in FIG. 2, each side corner area 33 is spaced by a distance D1 along the lamination direction from a corresponding lower end of the protective layer 4 (i.e., an upper end of the surface area 5 on a side surface 100 of the unit structure 10). Each side corner area 33 is spaced by a distance D2 along the lamination direction from a corresponding top surface 129 of the unit structure 10 (i.e., upper surface 129 of the layer 125) opposite to the bottom surface 320 of the heater 3 with respect to the electrolyte body 2. The uncovered surface area 5 is set such that a ratio D1/D2 of the distance D1 to the distance D2 is equal to or larger than 0.05 (D1/D2≧0.05).

The protective layer 4 is preferably formed of a lamination of a plurality of layer portions. In this embodiment, the protective layer 4 has an inner protective layer 41 (e.g., thickness of 20 μm) and an outer protective layer 42 (e.g., thickness of 50 μm). The inner layer 41 is directly disposed on the side surfaces of the layers 121, 124 and 125 and the electrolyte body 2, and the outer layer 42 is disposed on the inner layer 41 and is directly exposed to the measured gas. Size of particles of the outer layer 42 is set to be larger than that of the inner layer 41. Each of the protective layers 41 and 42 is, for example, made of at least one of γ-alumina, θ-alumina and titania ($TiO_2$) as a major material. An average size of the particles of the inner layer 41 is set within a range from 1 to 40 μm, and an average size of the particles of the outer layer 42 is set within a range from 2 to 100 μm. Particles of the alumina have a large specific surface area so as to effectively trap poisons of the measured gas on the surfaces of the particles.

The protective layer 4 preferably includes a catalyst so as to act as a catalytic layer. Various components (e.g., hydrogen having a high diffusion speed) not yet burned remain in the measured gas representing the exhaust gas. These non-burned components prevent the gas sensing member from precisely detecting a concentration of a specific component such as CO, NO, $O_2$ or the like. The catalyst accelerates the combustion of the non-burned components. In this embodiment, the inner layer 41 includes a catalyst made of a metal. For example, at least one of noble metals such as platinum (Pt), rhodium (Rh), ruthenium (Ru), palladium (Pd) and the like is used as the catalyst made of a metal. Because titania ($TiO_2$) has a catalyst performance, the inner layer 41 made of γ-alumina and/or θ-alumina as a major material may include titania ($TiO_2$) as a catalyst made of a metallic oxide. The noble metal acting as the catalyst preferably has an average size of particles set within a range from 0.01 to 5 μm. More preferably, the noble metal has an average size of particles set within a range from 0.1 to 2 μm. A catalyst content of the inner layer 41 is determined as follows. The measured gas passes through the layer 124 along a gas passing direction almost parallel to the width direction, before entering at each gas inlet 11. A portion of the inner layer 41 disposed on the gas inlet 11 has a projected area along a plane perpendicular to the gas passing direction. A catalyst content of the inner layer 41 is preferably set to be 10

μg/cm² or more per unit area of the projected area. More preferably, a catalyst content of the inner layer 41 is set within a range from 10 to 500 μg/cm² per unit area of the projected area.

The member 1 is, for example, obtained by sintering a unit of the electrolyte body 2 and the layers 121, 124 and 125, sintering the heater 3 separately from the unit, and attaching or contacting the sintered unit and the sintered heater 3 to each other. The heater 3 may be directly disposed on the electrolyte body 2. The electrode 21 may be disposed on the lower surface of the electrolyte body 2, while disposing the electrode 22 on the upper surface of the electrolyte body 2.

With this arrangement of the sensing member 1, when the driving of an engine is started, the heater 3 starts heating the electrolyte body 2, and the electrolyte body 2 is heated to the activate temperature so as to be activated. When a measured gas such as an exhaust gas output from the engine flows through an exhaust pipe, the measured gas is transmitted through the porous layer 124 disposed on the gas inlets 11 and enters at the gas inlets 11 before reaching the chamber 126. Therefore, the electrode 21 is indirectly exposed to the measured gas transmitted through the porous layer 124. Oxygen ions obtained by decomposing the measured gas or the reference gas passes through the electrolyte body 2 from one of the electrodes 21 and 22 to the other electrode, so that an electric potential difference is generated between the electrodes 21 and 22. Then, a concentration of a specific component (e.g., CO, NO, $O_2$ or the like) included in the measured gas is detected from the electric potential difference in a control section (not shown). Further, drops of water in the measured gas are attached on the whole surface of the gas sensing portion 1b of the member 1.

Because at least the gas inlets 11 are covered with the porous layer 4, poisons (e.g., components not yet burned) are removed from the measured gas entering into the chamber 126 by catalytic particles of the protective layer 4 when the measured gas goes through the gas inlets 11. Accordingly, the porous layer 4 disposed on the gas inlets 11 can protect the electrode 21 from poisons of the measured gas.

Further, the uncovered surface area 5 extends over the side corner areas 33 of the heater substrate 32 such that at least a portion of the side corner areas 33 is directly exposed to the measured gas. Accordingly, breakages and cracks of the member 1 can be reduced.

A mechanism for suppressing breakages and cracks of the member 1 will be described. When a thermal stress is generated in a portion of the heater substrate 32 corresponding to the side corner area 33, the thermal stress is easily concentrated in a narrow area so as to heighten a probability that the member 1 is broken or cracked. In this embodiment, the heater substrate 32 substantially has no water holding property, and at least a portion of each side corner area 33 is directly exposed to the measured gas. Therefore, even when drops of water are attached to one side corner area 33 heated at a high temperature, the drops of water are immediately detached from the side corner area 33 according to the Leidenfrost phenomenon so as to maintain the temperature of the side corner area 33. Accordingly, the generation of a thermal stress easily concentrated on the side corner area 33 can be prevented, and the side corner areas 33 directly exposed to the measured gas can prevents the sensing member 1 from being broken or cracked.

Especially, because all the side corner areas 33 are directly exposed to the measured gas, breakage or cracks of the sensing member 1 can be considerably reduced.

Moreover, assuming that a thermal stress is generated on the side corner area 330 of the heater substrate 32, the thermal stress is easily concentrated on an narrow area. However, in this embodiment, the side corner areas 33 and 330 directly exposed to the measured gas is set to be equal to or larger than 60% of the side corner areas 33 and 330 placed in the gas sensing portion 1b. Therefore, even when drops of water are attached to the side corner areas 330, the temperature of the side corner areas 330 can be reliably maintained due to the Leidenfrost phenomenon. Accordingly, the generation of a thermal stress easily concentrated can be suppressed, and breakages and cracks of the sensing member 1 can be further reduced.

Further more, because the bottom surface 320 and the front corner surface 34 of the heater substrate 32 are directly exposed to the measured gas, breakages and cracks in the heater substrate 32 can be further reduced.

Still further, assuming that the distance D1 from the side corner area 33 to the lower end of the protective layer 4 along the lamination direction and the distance D2 from the side corner area 33 to the top surface 129 of the unit structure 10 along the lamination direction is set to satisfy the ratio D1/D2 smaller than 0.05, the protective layer 4 is disposed near the side corner area 33. In this case, drops of water held in the protective layer 4 successively flow on the side surface 100 of the unit structure 10 and successively reaches the side corner area 33, so that there is a probability that a thermal stress will be generated in the side corner area 33 due to the water so as to generate breakages or cracks in the heater substrate 32. In contrast, in this embodiment, the ratio D1/D2 is set to be equal to or larger than 0.05. Accordingly, drops of water held in the protective layer 4 are vaporized before reaching the side corner area 33, so that breakages and cracks of the heater substrate 32 can be prevented.

Still further, because the protective layer 4 is not disposed on the whole surface of the unit structure 10, a thermal capacity of the sensing member 1 can be reduced to a small value. Accordingly, the electrolyte body 2 of the sensing member 1 can be quickly heated to its activation temperature, and a concentration of a specific component in the measured gas can be accurately detected even just after the driving of an engine is started.

Still further, because the protective layer 4 is formed of particles of γ-alumina or θ-alumina having a large specific surface area as a major material, poisons of the measured gas entering at the gas inlets 11 can be effectively trapped by the protective layer 4.

Still further, because the size of the particles in the outer layer 42 is set to be larger than that in the inner layer 41, poisons formed of particles of various sizes can be effectively trapped in the layers 41 and 42. More specifically, after poisons of larger sizes are trapped by the outer layer 42, poisons of smaller sizes are trapped by the upper layer 41. Further, assuming that the unit structure 10 is covered with a single porous protective layer having particles smaller than those of the outer layer 42, open spaces of the single porous protective layer are easily filled with large-sized poisons such as zinc oxide, calcium oxide, phosphorus oxide and/or the like. Therefore, the measured gas becomes hardly transmitted to the electrode 21 through the single porous protective layer. However, in this embodiment, the poisons are trapped by large particles of the outer layer 42 having large open spaces, and an amount of the poisons trapped in the inner layer 41 becomes low. Accordingly, the measured gas can reliably pass through the protective layers 41 and 42.

Still further, an average size of the particles of the inner layer 41 is set within a range from 1 to 40 μm, and an average size of the particles of the outer layer 42 is set within a range from 2 to 100 μm. Accordingly, gasoline additives such as lead (Pb), sulfur (S) and the like, oil additives such as calcium (Ca), phosphorus (P), silicon (Si), zinc (Zn) and the like, a gas of the gasoline additives and a gas of the oil additives can be effectively trapped in the protective layers 41 and 42.

Assuming that an average size of the particles of the inner layer 41 is smaller than 1 μm, open spaces between particles of the inner layer 41 become small. Therefore, the open spaces of the inner layer 41 are easily filled with a small amount of the additives of a gas state, and the speed of response of the gas sensing to a specific component of the measured gas is lowered at an earlier time. In contrast, assuming that an average size of the particles of the inner layer 41 is larger than 40 μm, the amount of additives in a gas state trapped in the inner layer 41 becomes low. Therefore, open spaces in the porous diffused resistor layer 124 are easily filled with the additives transmitted through the layers 41 and 42, or the additives are attached to the electrode 21.

Further, assuming that an average size of the particles of the outer layer 42 is smaller than 2 μm, open spaces between particles of the outer layer 42 become small. Therefore, the open spaces of the outer layer 42 are easily filled with a small amount of the oil additives, and a gas transmission performance of the outer layer 42 for the measured gas is lowered. As a result, the sensing member 1 cannot accurately detect a concentration of a specific component. In contrast, assuming that an average size of the particles of the outer layer 42 is larger than 100 μm, the open spaces of the outer layer 42 become too large, and an amount of the additives trapped in the outer layer 42 becomes low. Therefore, the open spaces of the porous diffused resistor layer 124 and the inner layer 41 are easily filled with the additives transmitted through the outer layer 42.

Still further, because the inner layer 41 of the protective layer 4 includes catalysts made of metal or metallic oxide, the poisons trapped by the inner layer 41 are efficiently decomposed. Accordingly, the poisons can further effectively be trapped by the inner layer 41. Moreover, because each particle of the major component in the inner layer 41 has a large specific surface area, a distance between catalysts of the inner layer 41 becomes large, and a holding force of the particles to the catalysts becomes strengthened. Accordingly, coagulation of the catalysts caused by the heat of the measured gas can be suppressed, and durability of the catalysts can be improved. That is, the catalysts can have a high heat-resistance.

Still further, the catalysts made of metal or metallic oxide can urge hydrogen gas included in the measured gas to be combined with oxygen gas of the measured gas. Therefore, the precision in the detection of a concentration of a specific component can be improved.

Still further, the catalysts are made of a noble metal of which particles have an average size set within a range from 0.01 to 5 μm. Accordingly, the inner protective layer 41 can sufficiently act as a catalyst layer superior in durability. Assuming that an average size of the noble metal is smaller than 0.01 μm, catalyst performance of the noble metal is rapidly degraded when the noble metal starts loosing the catalyst performance, so that precision of the detection in the gas sensing member is suddenly lowered. In contrast, assuming that an average size of the noble metal is larger than 5 μm, a specific surface area of the catalysts becomes too small, so that catalyst performance of the noble metal cannot sufficiently be obtained.

Still further, when an average size of the catalysts is set within a range from 0.1 to 2 μm, the inner protective layer 41 can further sufficiently act as a catalyst layer superior in durability.

Still further, the inner protective layer 41 includes catalysts made of titania. Accordingly, the inner protective layer 41 can sufficiently trap poisons as a catalyst layer.

Still further, a catalyst content is set to be 10 μg/cm$^2$ or more per unit area of a projected area which is determined by projecting the gas inlets 11 onto the surface of the gas measurement electrode 21. Accordingly, the inner protective layer 41 acting as a catalyst layer can efficiently trap poisons. Further, when a catalyst content is set within a range from 10 to 500 μg/cm$^2$ per unit area of the projected area, the poisons can efficiently be trapped while maintaining the speed of response of the gas sensing member 1. Assuming that the catalyst content is larger than 500 μg/cm$^2$ per unit area of the projected area, there is a possibility that poisons are excessively decomposed in the catalyst layer so as to degrade the speed of response of the gas sensing member.

As described above, in this embodiment, even though drops of water are attached to the sensing member 1, breakages and cracks of the sensing member 1 caused by the drops of water can be suppressed. Further, the sensing member 1 can rapidly reach a high temperature.

The inventors have conducted experiments to confirm effects obtained in the sensing member 1.

To conduct experiments, a gas sensing member having the side corner areas 33 not covered with the protective layer 4 but directly exposed to the atmosphere was prepared as a sample No. 1. The sample No. 1 represents the sensing member 1 shown in FIGS. 1 to 5. Further, samples No. 2, No. 3, No. 4 and No. 5 were prepared so as to be compared with the sample No. 1 in the experiments. Each of the samples No. 2 to No. 5 represents a gas sensing member having the side corner areas 33 wholly covered with the protective layer 4. The thickness of the protective layer 4 in the samples No. 2 to No. 5 is set to be 5 μm, 20 μm, 50 μm, and 80 μm, respectively.

In these experiments, water was dropped on a center area of the side corner area 33 in case of the sample No. 1, and water was dropped on an area of the protective layer 4 just over the center area of the side corner area 33 in case of each of the samples No. 2 to No. 5. Then, a level of temperature drop (ΔT) of the side corner area 33 caused by the dropped water was measured for each sample. A volume of the water was set at each of 0.1 μL and 0.2 μL for each sample. The temperature of the side corner area 33 in each sample was set at 700° C. before water dropping. The surface temperature was measured by using a thermo viewer. The measured results are indicated by Table 1.

TABLE 1

| Sample | Thickness of Porous Protective layer (μm) | Temperature Drop ΔT (° C.) | |
|---|---|---|---|
| | | Water Volume 0.1 μL | Water Volume 0.2 μL |
| No. 1 | 0 (No Layer) | 30 to 70 | 50 to 80 |
| No. 2 | 5 | 135 to 160 | 180 to 220 |
| No. 3 | 20 | 100 to 140 | 125 to 170 |
| No. 4 | 50 | 70 to 90 | 75 to 100 |
| No. 5 | 80 | 40 to 60 | 50 to 70 |

The thickness of the protective layer 4 denotes the sum of the thickness of the inner layer 41 and the thickness of the outer layer 42. The width of the unit structure 10 along the width direction is equal to 4.5 mm, and the thickness of the unit structure 10 along the lamination direction is equal to 2.0 mm.

In Table 1, maximum and minimum values of the temperature drop are indicated. As shown in Table 1, in case of the side corner area 33 directly exposed to the atmosphere, decrease of the temperature of the side corner area 33 caused by the dropped water of 0.1 μL is almost the same as that caused by the dropped water of 0.2 μL, and the temperature drop ranges from 30 to 80° C. In contrast, the temperature drop in case of the side corner area 33 covered with the protective layer 4 having the thickness of 5 μm, 20 μm or 50 μm becomes larger than that in case of the side corner area 33 directly exposed to the atmosphere. For example, the temperature drops corresponding to the thickness of 5 μm, 20 μm and 50 μm range from 135 to 220° C., from 100 to 170° C., and from 70 to 100° C., respectively.

Further, the temperature drop in case of the side corner area 33 covered with the protective layer 4 having the thickness of 80 μm is almost the same as that in case of the side corner area 33 directly exposed to the atmosphere. Therefore, when the side corner area 33 is covered with the protective layer 4 having the thickness of 80 μm or more, the temperature drop can be lowered. However, as the thickness of the protective layer 4 becomes large, a thermal capacity of the sensing member 1 is inevitably increased. In this case, even though a possibility of cracks or breakages in the sensing member is lowered, it takes a long time to heat the sensing member 1 when the driving of the engine is started, and the electrolyte body 2 of the sensing member 1 cannot rapidly reach its activity temperature. Therefore, it becomes difficult to accurately detect a concentration of a specific component included in a measured gas when the driving of the engine is started. Because emission regulations have become strict nowadays, it is strongly necessary for the electrolyte body 2 to rapidly reach its activity temperature for the purpose of lowering a volume of total hydrocarbons included in an exhaust gas when the driving of the engine is started.

After dropping the water on each sample, the inventors have observed the side corner area 33 to find out cracks generated in the heater substrate 32. Ten gas sensing members are prepared for each sample. The number Nc of members, wherein cracks are generated, is counted for each sample. A percentage of crack generation is indicated in Table 2. The observed results are indicated by Table 2.

TABLE 2

| Sample | Thickness of Porous Protective layer (μm) | percentage of Crack Generation (%) | |
|---|---|---|---|
| | | Water Volume 0.1 μL | Water Volume 0.2 μL |
| No. 1 | 0 (No Layer) | 0 | 0 |
| No. 2 | 5 | 100 | 100 |
| No. 3 | 20 | 100 | 90 |
| No. 4 | 50 | 30 | 50 |
| No. 5 | 80 | 0 | 0 |

In Table 2, the percentage R(%) is calculated according to an equation R=(Nc/10)×100.

As shown in Table 2, no cracks are generated in case of the side corner area 33 directly exposed to the atmosphere. In case of the side corner area 33 covered with the protective layer 4, as the thickness of the protective layer 4 becomes smaller, the rate of generation of cracks is increased. In case of the side corner area 33 covered with the protective layer 4 having the thickness of 80 μm, no cracks are generated. That is, when drops of water are attached to the protective layer 4 having a large thickness, the water is dispersed into the protective layer 4 along directions parallel to the surface area of the protective layer 4 and is absorbed into the protective layer 4. Therefore, it would be recognized that the water hardly reaches the side corner area 33 so as to cause the temperature drop of the side corner area 33 to become small. However, in case of the side corner area 33 covered with the protective layer 4 having the thickness of 80 μm, it takes a long time to heat the electrolyte body 2 to its activity temperature.

Accordingly, to prevent the generation of cracks or breakages in the sensing member 1 while maintaining a rapid activation of the electrolyte body 2, the sensing member 1 having the side corner areas 33, of which at least a portion is directly exposed to the atmosphere or a measured gas, is useful.

Next, a method of manufacturing the gas sensing member 1 shown in FIG. 1 to FIG. 5 will be described with reference to drawings.

Figure 7:
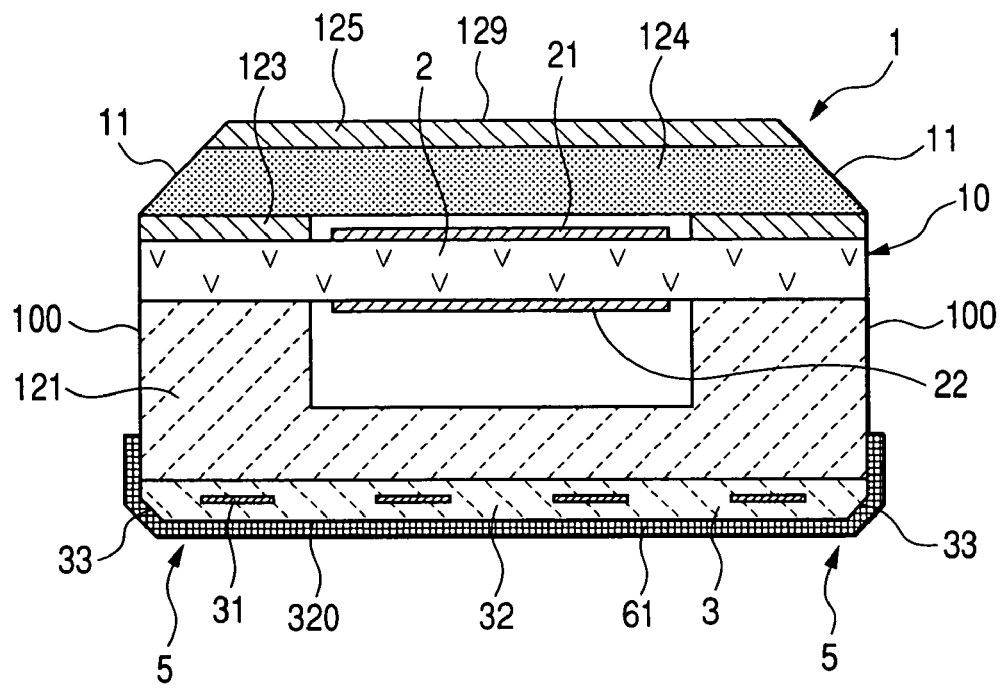
FIG. 7 is a vertical sectional view of a sensing member wherein a mask layer is formed on a surface of a unit structure to set an uncovered surface area.
Figure 8:
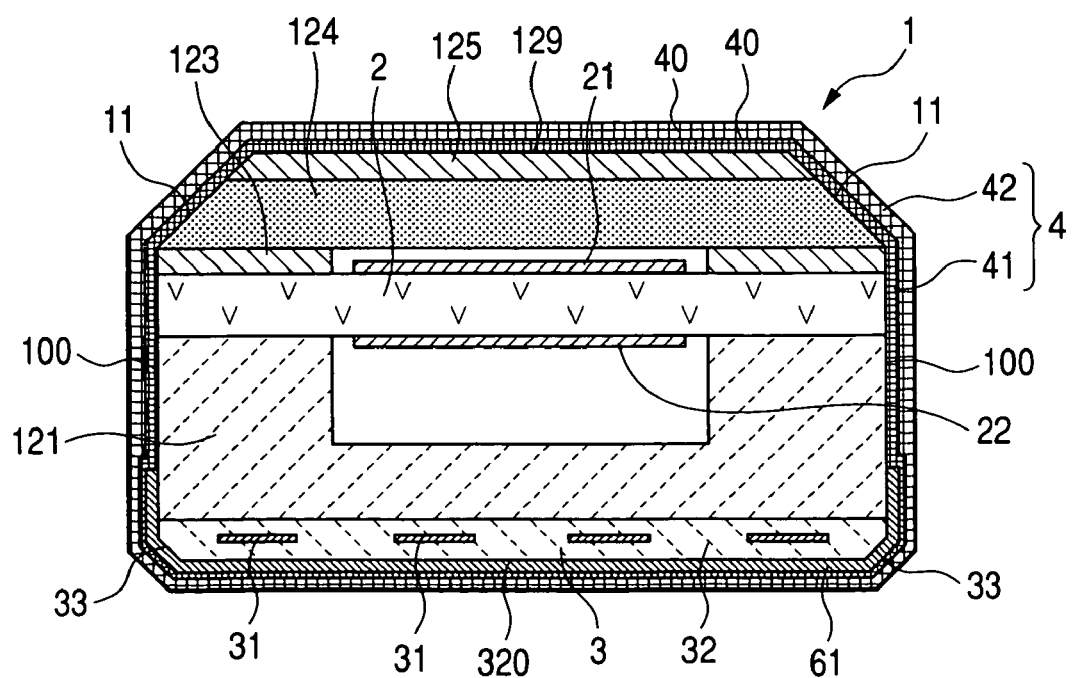
FIG. 8 is a vertical sectional view of a sensing member wherein the porous protective layer of a slurry state is attached on a whole surface of the sensing member shown in FIG. 7.

FIG. 6 is a flow chart showing a method of manufacturing the sensing member 1 according to the first embodiment. FIG. 7 is a vertical sectional view of the sensing member 1 wherein a mask layer is formed on a surface of the unit structure 10 to set the uncovered surface area 5. FIG. 8 is a vertical sectional view of the sensing member 1 wherein the protective layer 4 of a slurry state is attached on the whole surface of the unit structure 10 shown in FIG. 7.

As shown in FIG. 6, in a method of manufacturing the sensing member 1, the unit structure 10 is first assembled (step S0). Then, a first method of forming the porous protective layer 4 on the unit structure 10 is performed at steps S1 to S7. That is, as shown in FIG. 7, a mask layer 61 made of an organic material is formed on the side corner areas 33 and 330, the bottom surface 320 and the front corner surface 34 of the heater substrate 32 and parts of side surfaces of the chamber forming layer 121 near the heater substrate 32 in the gas sensing portion 1b of the sensing member 1 (step S1). The area of the mask layer 61 coincides with the uncovered surface area 5.

Then, as shown in FIG. 8, a protective layer forming material 40 formed in a slurry state is twice attached on the whole surface of the unit structure 10 including the gas inlets 11 of the portion 1b and is dried (steps S2 to S5). The mask layer 61 is covered with two layers of forming material 40.

Then, as shown in FIG. 6, a thermal treatment is performed for the sensing member 1 covered with the forming material 40 to bake the forming material 40 (step S6). In this treatment, the forming material 40 not disposed on the mask layer 61 is baked so as to form the protective layer 4, and the mask layer 61 is burned off so as to remove the baked forming material 40 disposed on the mask layer 61 from the sensing member 1. Therefore, the sensing member 1 shown in FIGS. 1 and 2 is obtained.

The method of forming the protective layer 4 is described in more detail. At step S1, a binder made of an acrylic material, cellulose or the like is dissolved with organic solvent to form a paste of a mask material 610. Then, the mask material 610 is coated on the uncovered surface area 5 according to pad transferring process, and the mask material 610 on the uncovered surface area 5 is dried, if necessary. Therefore, as shown in FIGS. 7 to 8, the mask layer 61 is formed on the sensing member 1.

At step S2, the unit structure 10 of the gas sensing portion 1b is dipped into a slurry of an inner protective layer forming material and is lifted up from the slurry. Therefore, the unit structure 10 is coated with the inner protective layer forming material.

At step S3, the material coated on the unit structure 10 is dried.

At step S4, the unit structure 10 is dipped into a slurry of an outer protective layer forming material and is lifted up from the slurry. Therefore, the unit structure 10 is coated with the outer protective layer forming material in addition to the inner protective layer forming material.

At step S5, the outer protective layer forming material coated on the unit structure 10 is dried.

At step S6, a thermal treatment is performed for the unit structure 10 coated with the mask layer 61 and the outer and inner protective layer forming materials at a temperature ranging from 500 to 1000° C. Therefore, the outer and inner protective layer forming materials are formed into the porous protective layer 4, and the mask layer 61 formed of a resin film is thermally decomposed and taken off from the unit structure 10. In this case, the porous protective layer 4 disposed on the mask layer 61 thermally decomposed is placed on the surface of the unit structure 10 at a very low attaching strength to the unit structure 10.

At step S7, the porous protective layer 4 disposed on the mask layer 61 thermally decomposed is removed from the unit structure 10 by an air blow or vibration.

Accordingly, the porous protective layer 4 can be precisely formed on a surface of the unit structure 10 except for the uncovered surface area 5, according to the first method of forming the protective layer 4.

A paste including a ultraviolet-ray curing resin may be used as the mask material 610. In this case, after the mask material 610 is transferred on the uncovered surface area 5 of the unit structure 10, the mask material 610 disposed on the unit structure 10 is irradiated with a ultraviolet ray, and the mask material 610 is cured so as to form the mask layer 61. The mask material 610 may be formed of a mixture of acrylic resin and/or α-terpineol ($C_{10}H_{18}O$) as a major material, a small amount of dispersing agent, a small amount of viscosity stabilizer, and a small amount of dye having a distinguishable color. The dye is contained in the mask material 610 to distinguish the mask material 610 coated on the uncovered surface area 5 from the surface of the unit structure 10. Therefore, the coated mask material 610 can be easily recognized by an operator, or image recognition of the coated mask material 610 can be easily performed by using a camera.

Figure 9:
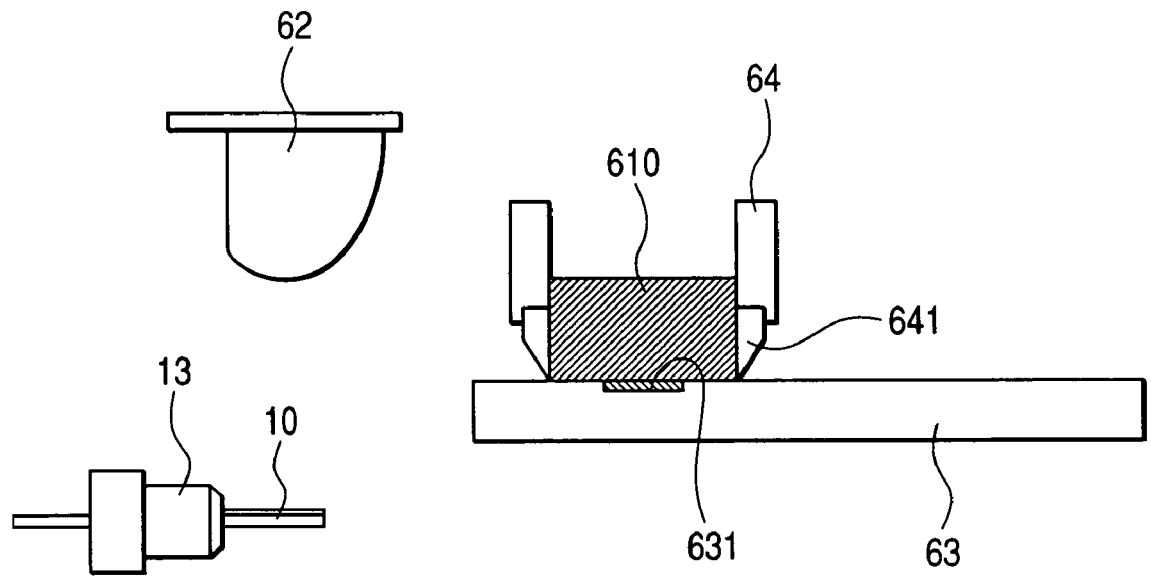
FIG. 9 is a first view explanatorily showing a pad transferring process performed for the sensing member.
Figure 10:
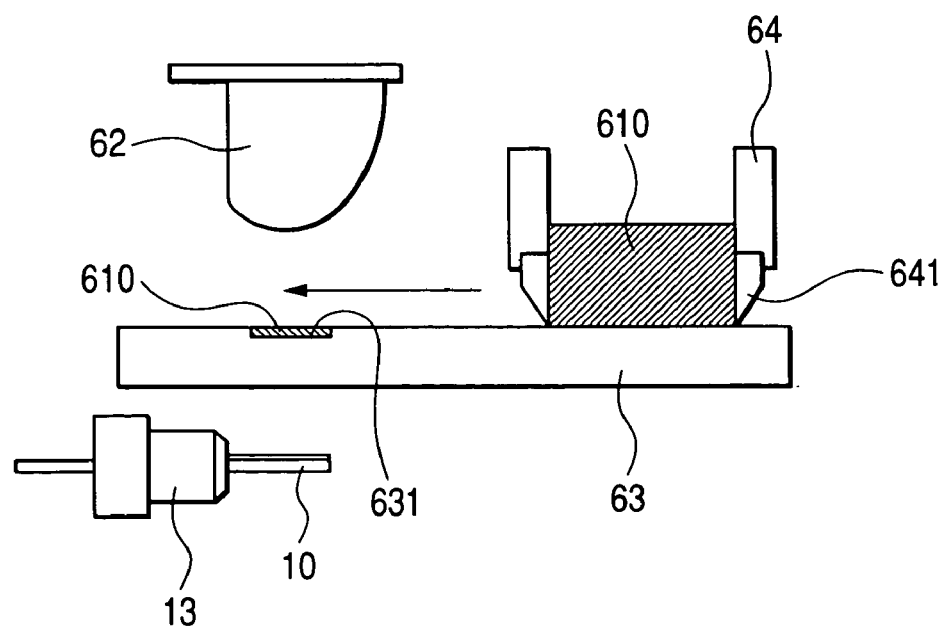
FIG. 10 is a second view explanatorily showing the pad transferring process.
Figure 11:
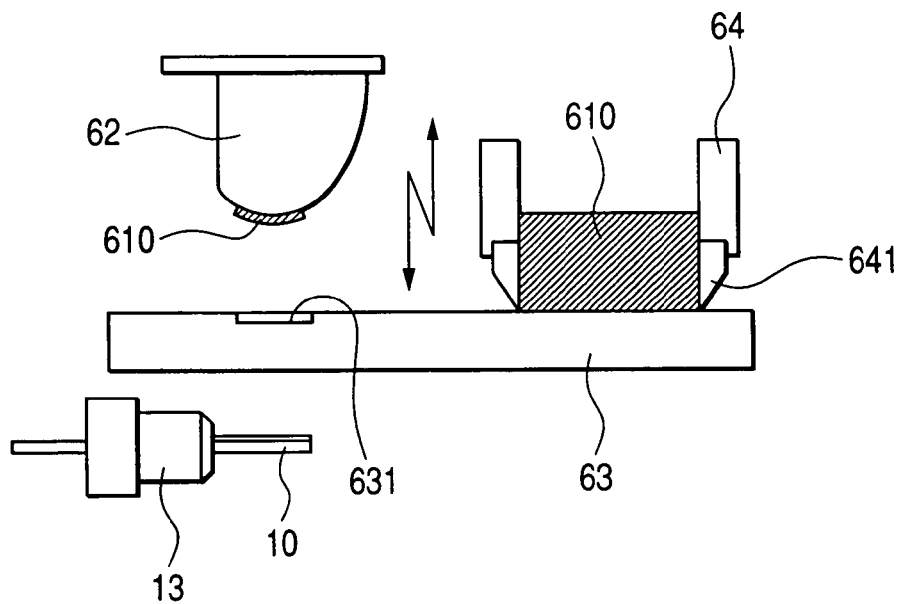
FIG. 11 is a third view explanatorily showing the pad transferring process.
Figure 12:
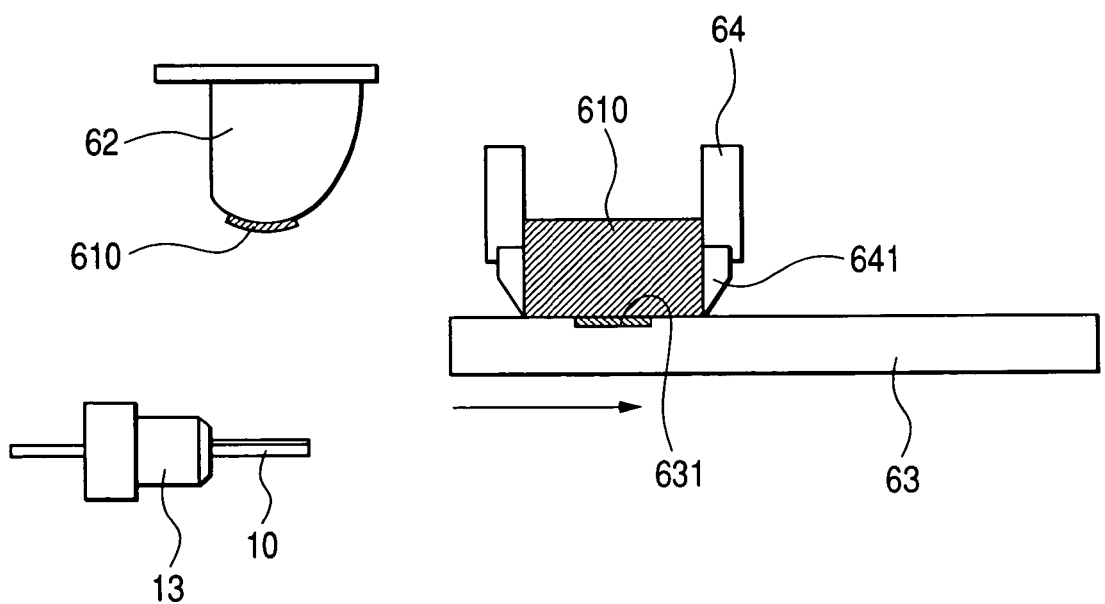
FIG. 12 is a fourth view explanatorily showing the pad transferring process.
Figure 13:
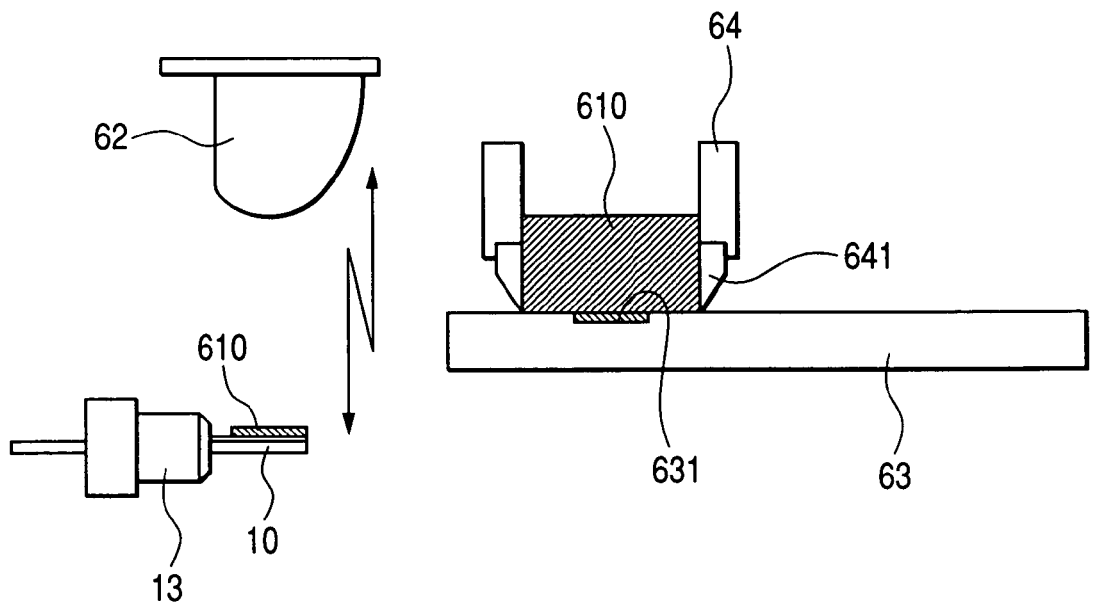
FIG. 13 is a fifth view explanatorily showing the pad transferring process.
Figure 14:
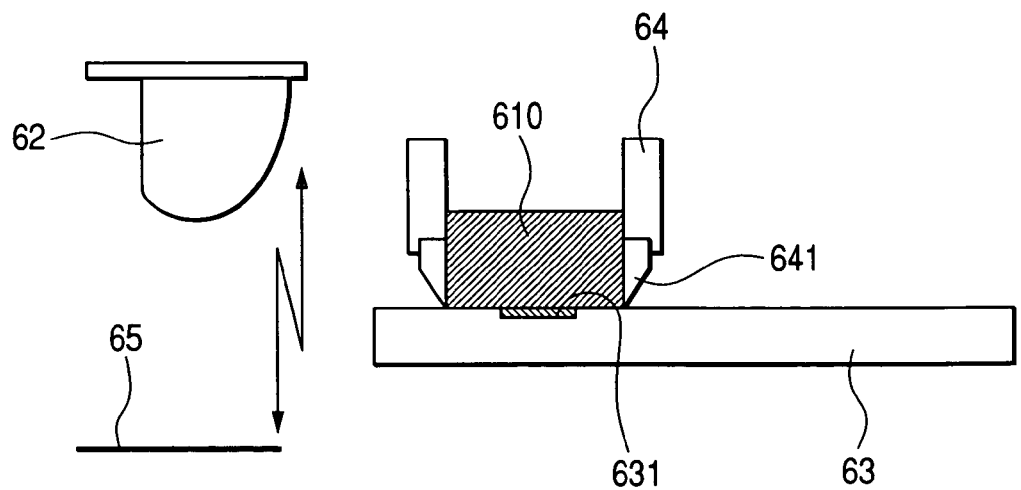
FIG. 14 is a sixth view explanatorily showing the pad transferring process.

The pad transferring process for the mask material 610 at step S1 is described in detail with reference to FIGS. 9 to 14. FIG. 9 is a first view showing a pad transferring process for the sensing member 1. FIG. 10 is a second view showing the pad transferring process. FIG. 11 is a third view showing the pad transferring process. FIG. 12 is a fourth view showing the pad transferring process. FIG. 13 is a fifth view showing the pad transferring process. FIG. 14 is a sixth view showing the pad transferring process.

In this pad transferring process, the mask material 610 is attached to a pad element and is transferred on the surface area 5 of the unit structure 10 before being dried. As shown in FIG. 9, to perform the pad transferring, an intaglio plate 63 having a concave space 631 on its upper surface, an ink pot 64 having a ring blade 641 slidable on the upper surface of the intaglio plate 63 and a pad element 62 made of rubber and formed in high flexibility are used. The concave space 631 has a size, shape and depth corresponding to the mask layer 61 to be disposed on the uncovered surface area 5. The ink pot 64 is filled with the mask material 610 and is placed on the concave space 631 of the intaglio plate 63. The intaglio plate 63 is placed at an original position. Then, the concave space 631 is filled with the mask material 610 poured from the ink pot 64.

Then, as shown in FIG. 10, the intaglio plate 63 is moved horizontally so as to place the concave space 631 under the pad element 62. The concave space 631 is filled with a predetermined volume of mask material 610. Then, as shown in FIG. 11, the pad element 62 is moved down so as to be attached to the intaglio plate 63. Then, the pad element 62 is moved up. Therefore, the mask material 610 of the concave space 631 is transferred to the pad element 62. Then, as shown in FIG. 12, the intaglio plate 63 is moved back to the original position. Then, as shown in FIG. 13, the pad element 62 is placed over the unit structure 10 which is inserted into and fixed to an insulator 13 of a gas sensor. Then, the pad element 62 is moved down so as to be attached to the unit structure 10. Then, the pad element 62 is moved up. Therefore, the mask material 610 of the pad element 62 is transferred to the unit structure 10. Then, as shown in FIG. 14, the pad element 62 is cleaned by using a cleaning tape 65, so that remaining materials attached to the pad element 62 are removed. This pad transferring process is performed for each of a plurality of elements 1 sequentially carried.

Effects obtained in the method of manufacturing the sensing member 1 are described.

Because the thermal treatment is performed for the sensing member 1 covered with the forming material 40, the forming material 40 is baked, while the mask layer 61 is burned off. Therefore, the porous protective layer 4 is formed of the baked forming material 40 not disposed on the mask layer 61, and the forming material 40 disposed on the mask layer 61 is removed from the sensing member 1. Accordingly, the protective layer 4 can be easily formed such that the gas inlets 11 are covered with the protective layer 4, and at least a portion of the side corner areas 33 of the heater substrate 32 can reliably be set as the uncovered surface area 5 not covered with the protective layer 4. Further, because the protective layer 4 and the side corner areas 33 not covered with the protective layer 4 are simultaneously obtained in the thermal treatment, efficiency in the manufacturing of the sensing member 1 can be improved.

Further, because the mask layer 61 is formed on a desired surface area of the unit structure 10 by transferring the mask material 610 attached to the pad element 62 to the desired surface area, the mask layer 61 can be easily and reliably formed on the unit structure 10 so as to set at least a portion of the side corner areas 33 as the uncovered surface area 5. Accordingly, this manufacturing method can be superior in productivity of the sensing member 1.

Moreover, because the pad element 62 is formed in high flexibility, the pad element 62 attached to the unit structure 10 is easily deformed on the surface of the unit structure 10. In this case, although a combined area of the side corner areas 33 and a part of the surfaces of the layer 121 adjacent to the side corner areas 33 is curved, the pad element 62 is easily deformed along the combined area. Accordingly, the mask material 610 can be easily and reliably formed on the combined area, so that the uncovered surface area 5 including a part of the surfaces of the layer 121 can be easily and efficiently set.

Furthermore, because the mask material 610 is formed of a ultraviolet-ray curing resin, the mask material 610 attached to the uncovered surface area 5 of the unit structure 10 is reliably hardened in a short time when being irradiated with ultraviolet rays. Therefore, the unit structure 10 can be coated with the protective layer forming material 40 in a short time after the uncovered surface area 5 of the unit structure 10 is coated with the mask material 610. Accordingly, efficiency in the manufacturing of the sensing member 1 can be further improved.

Embodiment 2

Another method of attaching the mask material 610 to the uncovered surface area 5 of the unit structure 10 at step S1 is described according to the second embodiment.

Figure 15:
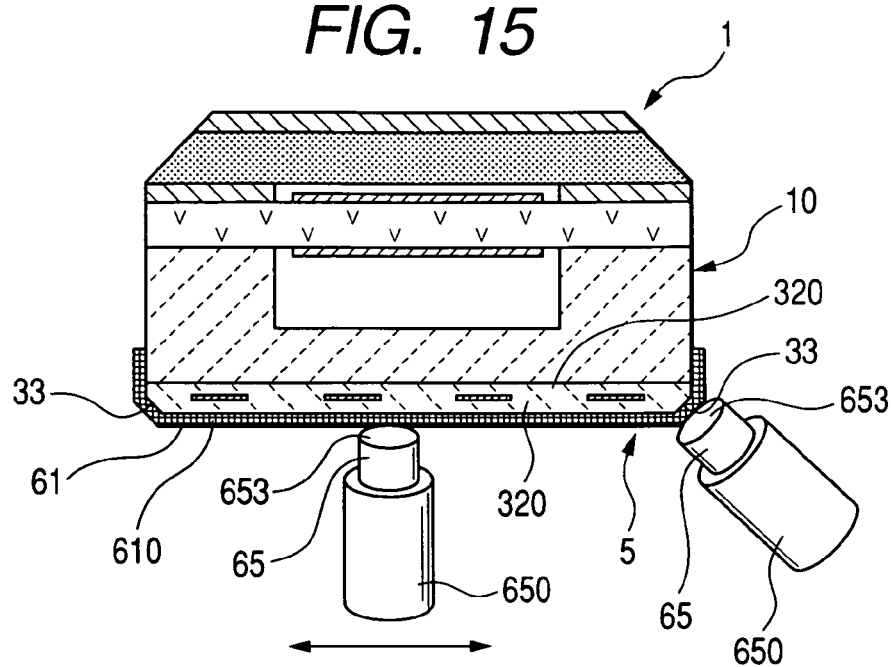
FIG. 15 is an explanatory view of a method of attaching a mask material to a unit structure according to the second embodiment.
Figure 16:
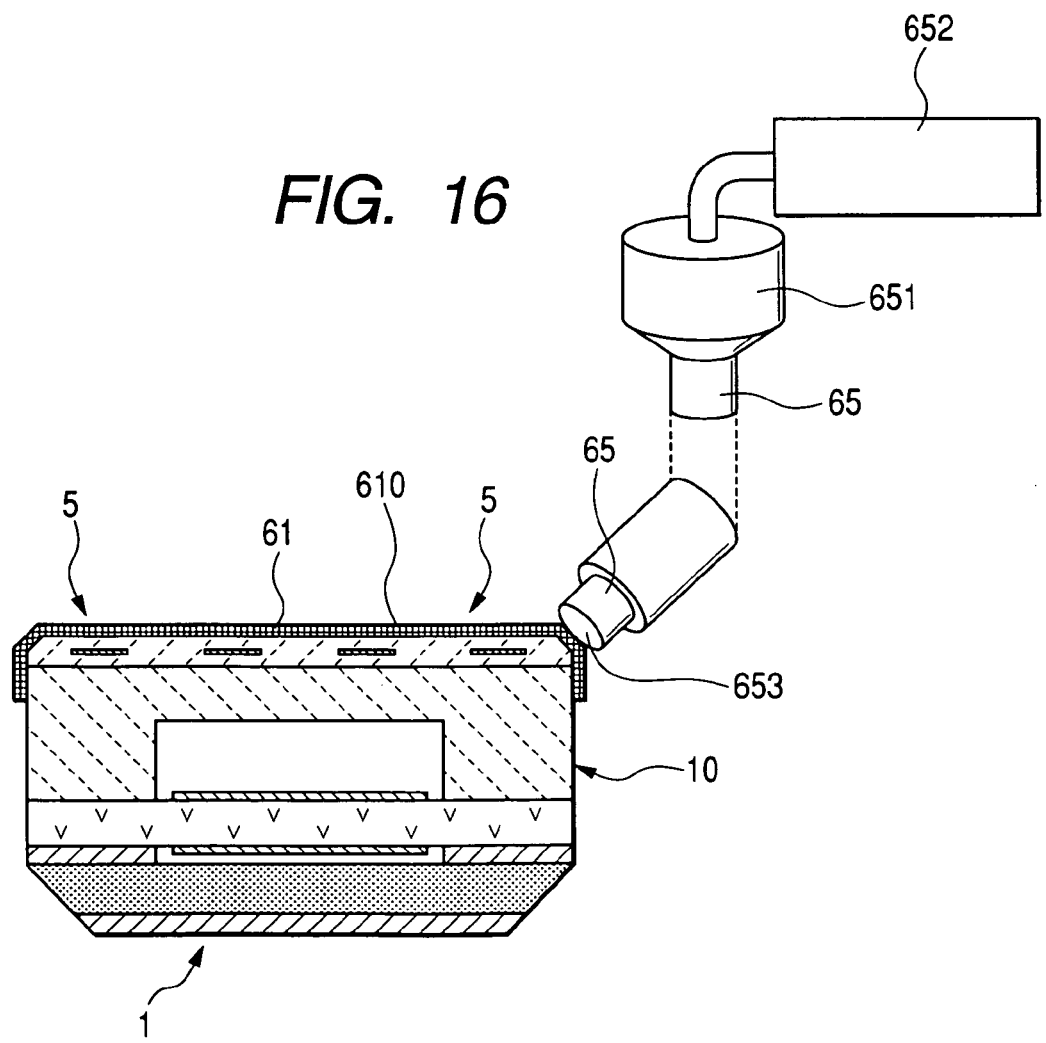
FIG. 16 shows a coating system used according to the second embodiment.
Figure 17:
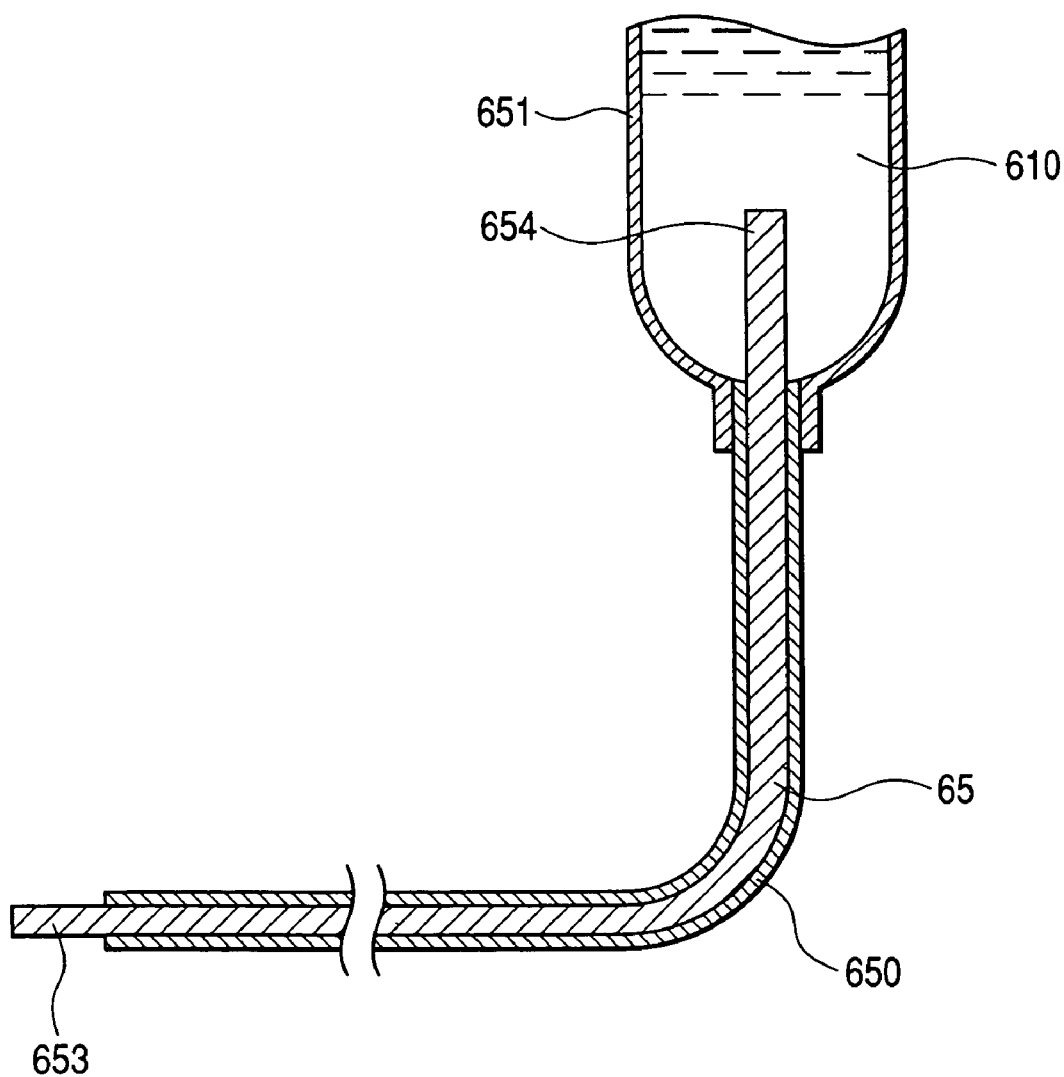
FIG. 17 is a sectional view of a nozzle tube and a tank of the coating system shown in FIG. 16.

FIG. 15 is an explanatory view of a method of attaching the mask material 610 to the unit structure 10 according to the second embodiment. FIG. 16 shows a coating system used according to the second embodiment. FIG. 17 is a sectional view of a nozzle tube and a tank of the coating system shown in FIG. 16.

As shown in FIG. 15, a porous felt element 65 is held in an inner open space of a nozzle tube 650 and is impregnated with a paste of the mask material 610 including resin. A top portion 653 of the felt element 65 projected from a tip of the nozzle tube 650 comes in contact with a surface of the unit structure 10 and is moved on an uncovered surface area 5 of the unit structure 10. During the movement of the felt element 65, the mask material 610 is automatically attached to the uncovered surface area 5 of the unit structure 10 according to the capillary phenomenon. Therefore, the uncovered surface area 5 of the unit structure 10 can be coated with the mask material 610, as if the uncovered surface area 5 is marked by using a felt pen.

More specifically, as shown in FIGS. 16 and 17, the nozzle tube 650 is connected with a pressure adjusting device 652 through a tank 651. The mask material 610 is stocked in the tank 651, and the device 652 adjusts the pressure of the tank 651. The felt element 65 is formed in a string shape, and a proximal portion 654 of the felt element 65 is disposed within the tank 651. An amount of the mask material 610 supplied to the felt element 65 is adjusted by increasing or decreasing the pressure of the tank 651. The device 652 adjusts the pressure of the tank 651 in accordance with physical properties of the mask material 610 such as viscosity and the like. Therefore, a flow rate of the mask material 610 output from the felt element 65 can precisely be adjusted. Accordingly, in addition to the effects in the first embodiment, the mask material 610 can reliably be attached to the uncovered surface area 5 of the unit structure 10 without being attached to an area out of the uncovered surface area 5 or being insufficiently attached to the uncovered surface area 5.

In this embodiment, the proximal portion 654 of the felt element 65 may be disposed in the middle of the nozzle tube 650. Further, the felt element 65 is formed in a columnar shape. However, the shape of the felt element 65 may properly be determined dependent on the shape of the uncovered surface area 5. Moreover, the top portion 653 of the felt element 65 may be away from the surface of the unit structure 10 by a small distance.

Embodiment 3

Another method of manufacturing the gas sensing member 1 shown in FIG. 1 will be described.

Figure 18:
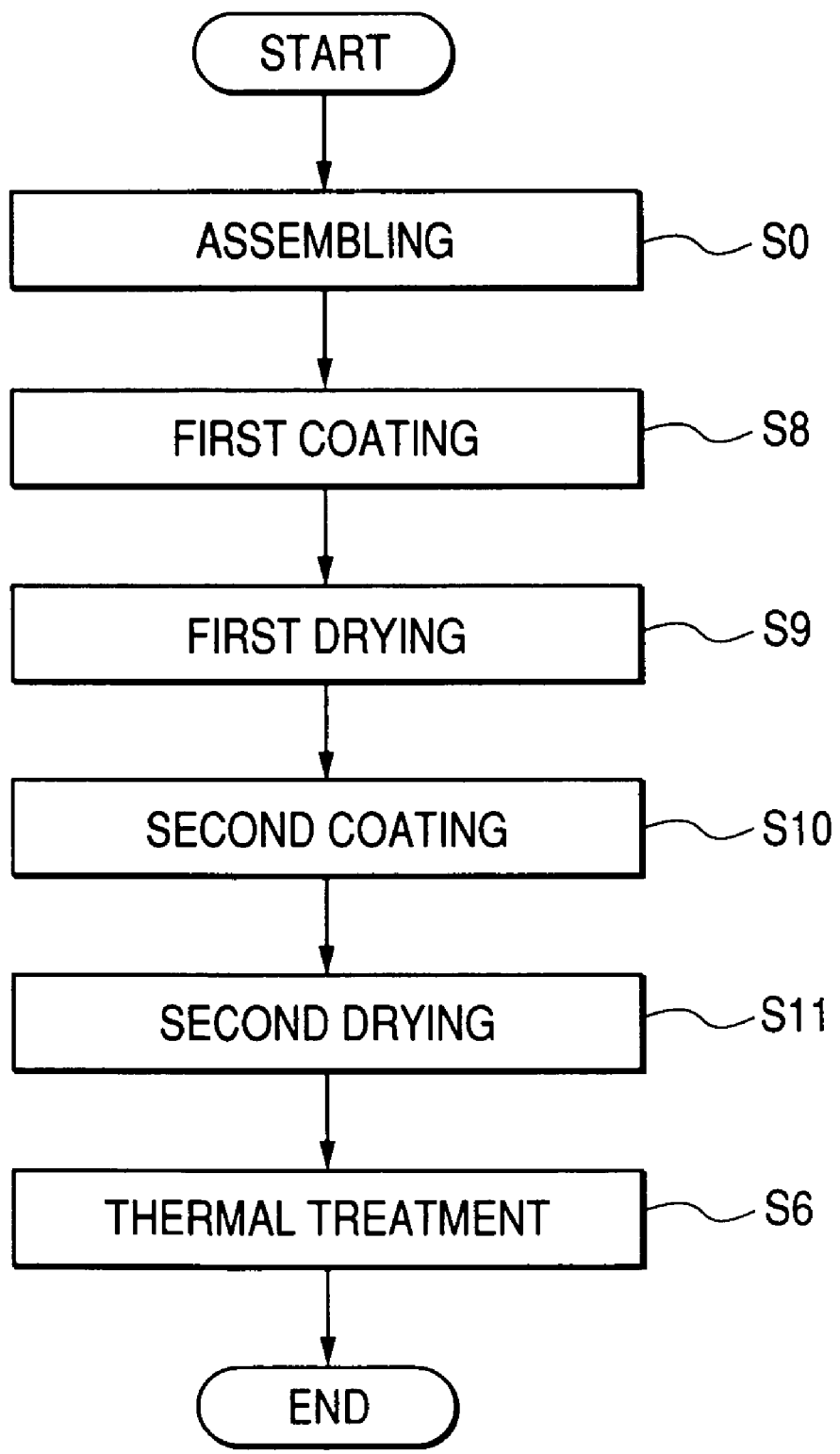
FIG. 18 is a flow chart showing a method of manufacturing the sensing member shown in FIG. 1 to FIG. 5 according to third to fifth embodiments of the present invention.
Figure 19:
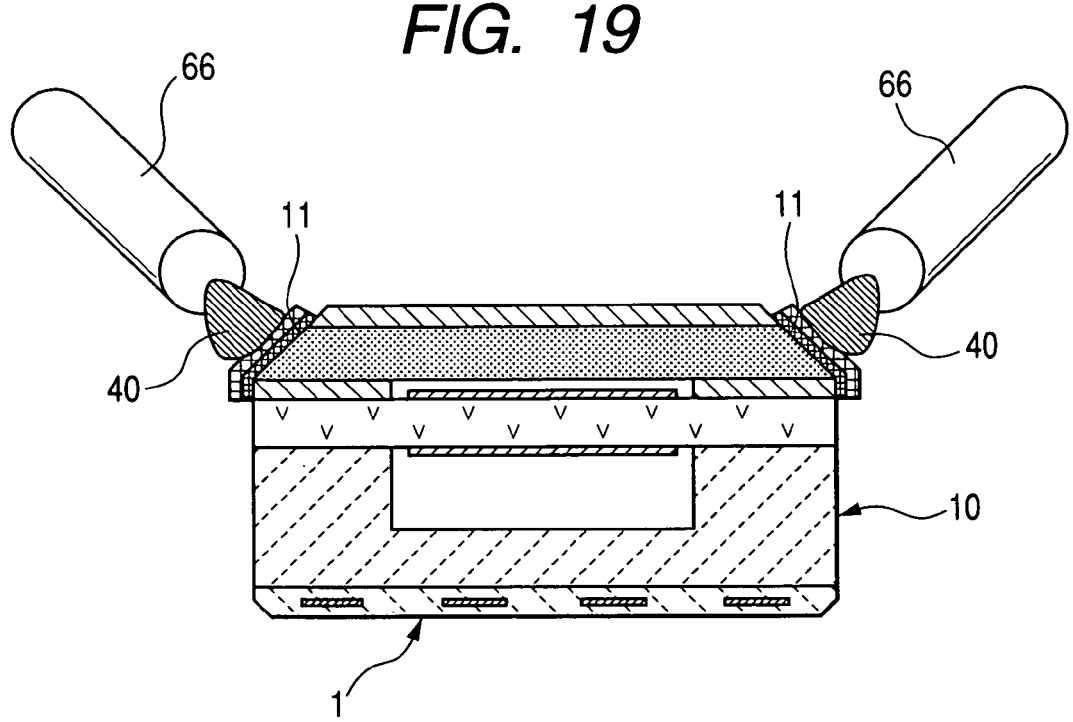
FIG. 19 is an explanatory view showing a method of attaching a protective layer forming material to a unit structure by using a dispenser according to the third embodiment.
Figure 20:
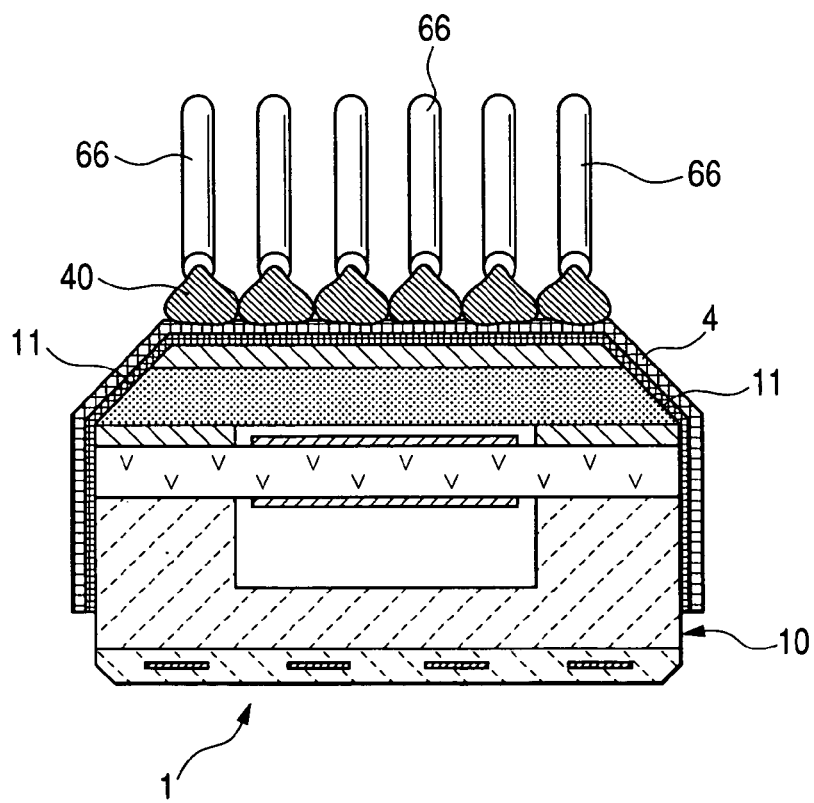
FIG. 20 is an explanatory view showing another method of attaching a protective layer forming material to a unit structure according to a modification of the third embodiment.

FIG. 18 is a flow chart showing a method of manufacturing the sensing member 1 shown in FIG. 1 to FIG. 5 according to third to fifth embodiments. FIG. 19 is an explanatory view showing a method of attaching the protective layer forming material 40 to the unit structure 10 by using a dispenser, according to the third embodiment. FIG. 20 is an explanatory view showing another method of attaching the protective layer forming material 40 to the unit structure 10, according to a modification of the third embodiment.

In this method, as shown in FIG. 18, the unit structure 10 is first assembled at step S0. Then, a second method of forming the protective layer 4 on a coating surface area of the unit structure 10 is performed. More specifically, the forming material 40 is set to be in a paste or slurry state. Thereafter, as shown in FIG. 19, at steps S8 and S10, the gas inlets 11 of the unit structure 10 are directly coated twice with the forming material 40 by using a dispenser 66, and the forming material 40 is dried at steps S9 and S11. Thereafter, at step S6, a thermal treatment is performed for the forming material 40 attached to the unit structure 10 to form the protective layer 4 on the unit structure 10.

Therefore, because the unit structure 10 is coated with the forming material 40 by using the dispenser 66, it is possible to precisely adjust volume and flow rate of the forming material 40 discharged from the dispenser 66. Accordingly, the forming material 40 attached to the unit structure 10 can precisely be set in shape, area and thickness.

Further, the diameter of a discharging outlet of the dispenser 66 can arbitrarily be adjusted, as well as the movement of the dispenser 66 on the surface of the unit structure 10. Accordingly, the dispenser 66 can form the protective layer 4 in a complicated shape.

This method is not limited to the usage of a single dispenser. As shown in FIG. 20, a plurality of dispensers 66 may be used to directly coat a wider coating surface area of the unit structure 10 with the forming material 40. Accordingly, the forming material 40 can quickly be attached to a large area of the surface of the unit structure 10, and productivity of the sensing member 1 can be improved, in addition to the effects in the third embodiment.

Embodiment 4

Another method of attaching the forming material 40 to the unit structure 10 is described.

FIG. 21 is an explanatory view showing a method of attaching the forming material 40 to the unit structure 10 according to the fourth embodiment.

As shown in FIG. 21, after the forming material 40 is set to be in a paste or slurry state, the coating surface area of the unit structure 10 is coated with the forming material 40 at steps S8 and S10 by spraying the coating surface area with the forming material 40 discharged from a nozzle 67. Then, the forming material 40 is dried at steps S9 and S11, and a thermal treatment is performed for the forming material 40 at step S6. Accordingly, even though the coating surface area of the unit structure 10 is formed in an uneven shape, the forming material 40 can easily and reliably be attached on the coating surface area of the unit structure 10.

Embodiment 5

Another method of attaching the forming material 40 to the unit structure 10 is described.

FIG. 22 is an explanatory view showing a method of attaching the forming material 40 to the unit structure 10 according to the fifth embodiment.

In this method, the forming material 40 is set to be in a paste state, and a concave space of an intaglio plate (not shown) is filled with the forming material 40, and the forming material 40 is attached to a pad element 68 made of rubber and formed in high flexibility. Thereafter, as shown in FIG. 22, the coating surface area of the unit structure 10 is coated with the forming material 40 at steps S8 and S1 by transferring the forming material 40 attached to the pad element 68 to the coating surface area. Then, the forming material 40 is dried at steps S9 and S11, and a thermal treatment is performed for the forming material 40 at step S6.

In this method, even though the coating surface area is formed in a complicated shape, the surface of the pad element 68 is easily deformed along the shape of the coating surface area. Accordingly, the forming material 40 having a predetermined size can correctly be attached on a predetermined surface area of the unit structure 10.

Further, the thickness of the forming material 40 attached to the pad element 68 can precisely be set by adjusting the depth of the concave space of the intaglio plate. Accordingly, the forming material 40 can be attached to the unit structure 10 at a predetermined thickness. Moreover, because the intaglio plate can have the concave space set at a uniform depth, the forming material 40 attached to the unit structure 10 can easily be set in a uniform thickness.

The forming material 40 may be attached to the unit structure 10 in accordance with a screen printing process. In this method, the forming material 40 having a predetermined size can correctly be attached on a predetermined surface area of the unit structure 10.

Embodiment 6

Another gas sensing member will be described with reference to FIG. 23.

Figure 23:
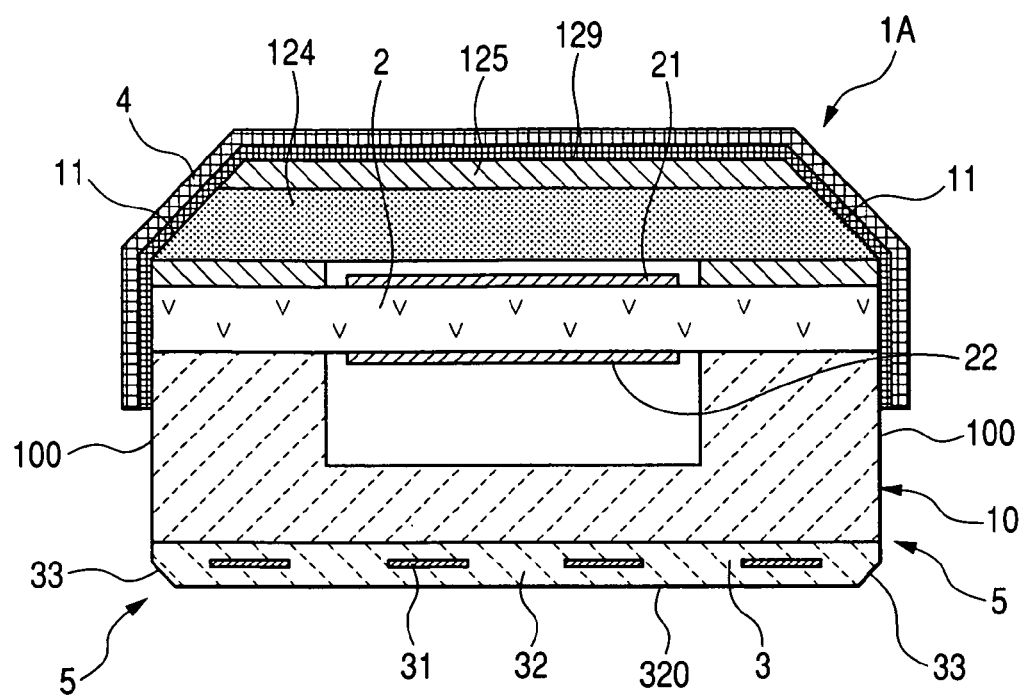
FIG. 23 is a vertical sectional view of a gas sensing member according to the sixth embodiment of the present invention.

FIG. 23 is a vertical sectional view of a gas sensing member according to the sixth embodiment of the present invention. As shown in FIG. 23, a gas sensing member 1A in the sixth embodiment has the same unit structure 10 as that of the sensing member 1 in the first embodiment. The member 1A differs from the sensing member 1 in that the ratio D1/D2 in the sensing member 1A is set to be almost 0.5.

As compared with the side corner areas 33, the side surface 100 of the unit structure 10 has a higher anti-water property. That is, even though water is attached on the side surface 100, a probability of generation of cracks or breakages in the unit structure 10 is lower than that in cases where water is attached on the side corner areas 33. However, stress is easily concentrated at many positions of the side surface 100, and generation of cracks or breakages is started from the stress concentrating positions in high degree. For example, when the unit structure 10 is sintered or baked during the formation of the unit structure 10, small defect portions are generated on the side surface 100, and stress is easily concentrated on the defect portions. Therefore, to prevent the generation of cracks or breakages in the unit structure 10, it is better to expose a larger part of the side surface 100 to the atmosphere or the measured gas. Even though water is directly attached on the side surface 100, the temperature drop of the side surface 100 can become small due to the Leidenfrost phenomenon.

Accordingly, because the ratio D1/D2 is set to be almost 0.5 so as to cover almost a half portion of the side surface 100 with the protective layer 4, a probability of the generation of cracks or breakages caused on the side surface 100 can be reduced.

The sensing member 1A may be manufactured according to any of the methods described in the first to fifth embodiments, in the same manner as the sensing member 1.

The inventors have conducted experiments to examine a relation between the ratio D1/D2 and a percentage of generation of cracks in a gas sensing member. To conduct experiments, a gas sensing member wholly covered with the protective layer 4 (D1/D2=0) was prepared as a sample No. 1. Further, gas sensing members set at the ratios D1/D2=0.02, D1/D2=0.05, D1/D2=0.10, D1/D2=0.20, D1/D2=0.40, and D1/D2=0.70 are prepared as samples No. 2, No. 3, No. 4, No. 5, No. 6 and No. 7, respectively. A thickness of the protective layer 4 is set at 5 μm. Water is dropped on the uncovered surface area 5 (samples No. 2 to No. 7) or dropped on the protective layer 4 disposed on the uncovered surface area 5 (sample No. 1). A volume of dropped water was set at each of 0.1 μL. The percentage of crack generation is calculated in the same manner as that shown in Table 2. The porous diffused resistor layer 124 is disposed to be far from the side corner areas 33 by a distance of 0.75×D2. Examined results are indicated in Table 3.

TABLE 3

| Sample | D1/D2 | Percentage of Crack Generation (%) |
|---|---|---|
| No. 1 | 0 | 100 |
| No. 2 | 0.02 | 30 |
| No. 3 | 0.05 | 0 |
| No. 4 | 0.10 | 0 |
| No. 5 | 0.20 | 0 |
| No. 6 | 0.40 | 0 |
| No. 7 | 0.70 | 0 |

As shown in Table 3, in case of D1/D2 equal to or smaller than 0.02, cracks are generated in the unit structure 10. The reason is as follows. The protective layer 4 disposed on the side surface 100 is close to the side corner area 33. In the first reason, water held in the protective layer 4 reaches the side corner area 33 and acts to generate a thermal stress in the side corner area 33, so that cracks are generated on the side corner area 33. In the second reason, when water is attached on the side corner area 33, a portion of water is vaporized due to the Leidenfrost phenomenon, and the other portion of water is dispersed on the side corner area 33 and is held in the protective layer 4 so as to quickly lower the temperature of the side surface 100. Therefore, cracks are generated at stress concentrating positions of the side surface 100.

In contrast, in case of D1/D2 equal to or larger than 0.05, no cracks are generated in the unit structure 10. The reason is as follows. The protective layer 4 disposed on the side surface 100 is placed sufficiently far from the side corner area 33. In the first reason, even though water is held in the protective layer 4, the water does not reach the side corner area 33. Therefore, no cracks are generated on the side corner area 33. In the second reason, when water is attached on the side corner area 33, the water hardly reach the protective layer 4, so that the temperature of the side surface 100 can be maintained at a high temperature. The temperature drop of the side corner area 33 is suppressed due to the Leidenfrost phenomenon. Therefore, no cracks are generated in the sensing member.

Accordingly, when the protective layer 4 is disposed on the side surface 100 of the unit structure 10 so as to satisfy the ratio D1/D2 equal to or larger than 0.05, generation of cracks and breakages in the sensing member can further be suppressed.

Embodiment 7

Figure 24:
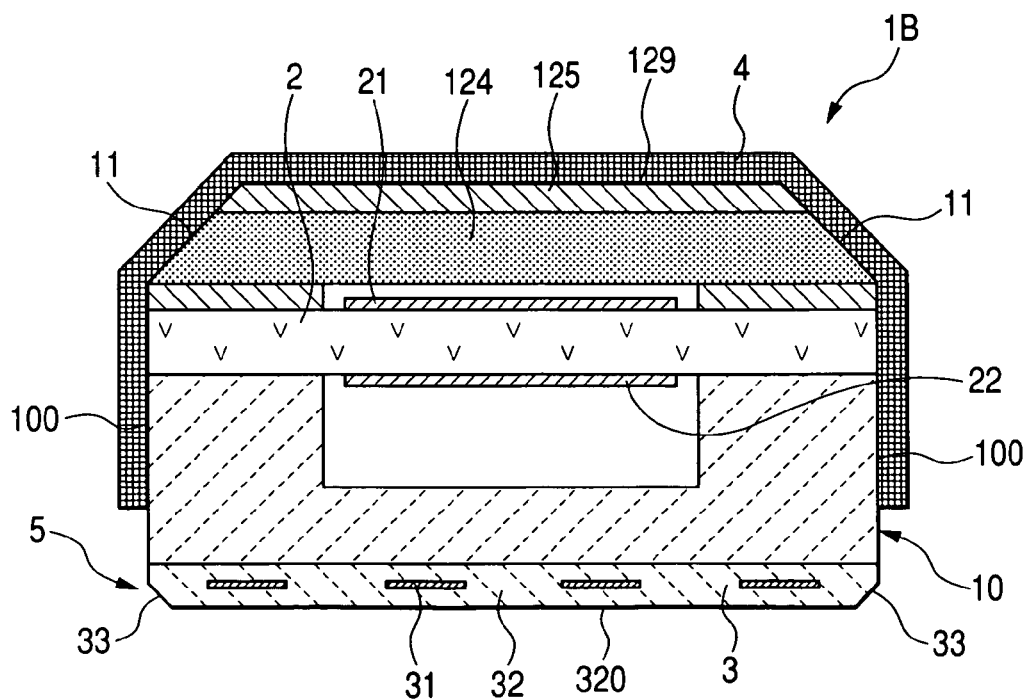
FIG. 24 is a vertical sectional view of a gas sensing member according to the seventh embodiment of the present invention.

FIG. 24 is a vertical sectional view of a gas sensing member according to the seventh embodiment of the present invention. As shown in FIG. 24, a gas sensing member 1B in the seventh embodiment has the same unit structure 10 as that of the sensing member 1 in the first embodiment. The sensing member 1B differs from the sensing member 1 in that the protective layer 4 has only a single layer.

Accordingly, as compared with the sensing member 1 shown in FIGS. 1 to 5, although the sensing member 1B is slightly inferior to the performance of trapping poisons of the measured gas, breakages and cracks in the sensing member 1B caused by water attached to the sensing member 1B can be suppressed in the same manner as in the sensing member 1 while a heat capacity of the sensing member 1B is maintained to a low level. Further, as compared with the sensing member 1, the sensing member 1B can easily be manufactured according to any of the methods described in the first to fifth embodiments.

Embodiment 8

Figure 25:
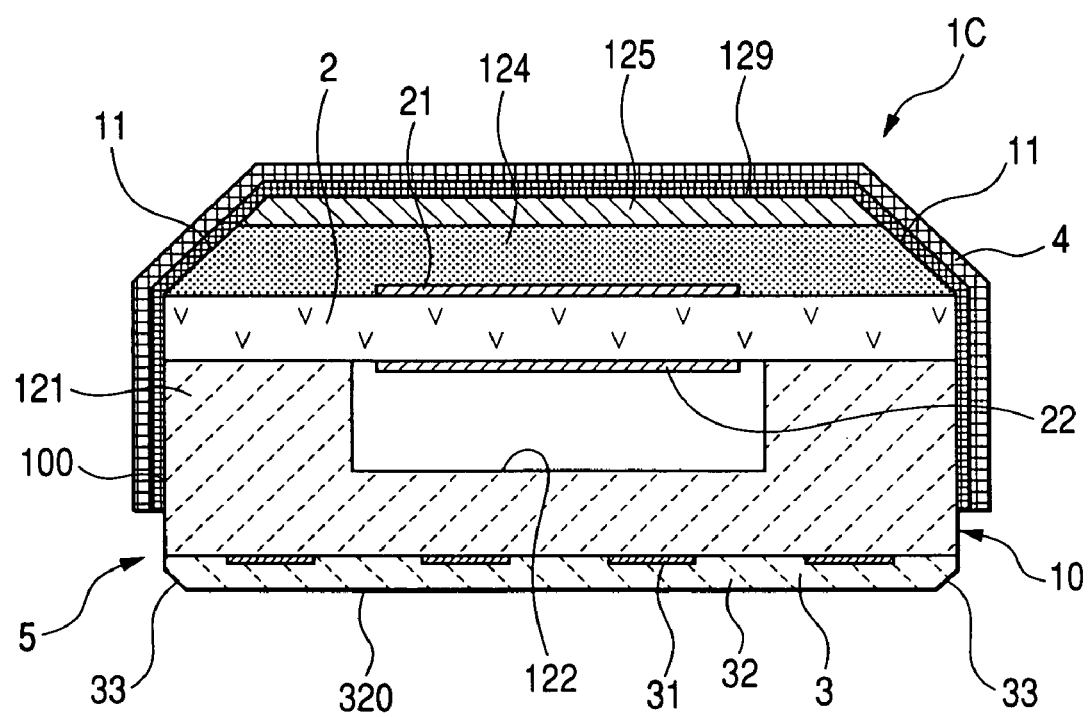
FIG. 25 is a vertical sectional view of a gas sensing member according to the eighth embodiment of the present invention.

FIG. 25 is a vertical sectional view of a gas sensing member according to the eighth embodiment of the present invention.

As shown in FIG. 25, a gas sensing member 1C in the eighth embodiment has the same unit structure 10 as that of the sensing member 1 in the first embodiment. The sensing member 1C differs from the sensing member 1 in that the gas measurement electrode 21 is directly in contact with the porous diffused resistor layer 124, and the heating elements 31 buried in the heater substrate 32 are directly in contact with the chamber forming layer 121.

In this arrangement of the sensing member 1C, although the sensing member 1 in the first embodiment has the measured gas chamber 124 and the spacer 123, the sensing member 1C does not have the gas chamber 124 or the spacer 123. Accordingly, the manufacturing of the sensing member 1C can be simplified.

Further, because the heating elements 31 is disposed so as to be in contact with the chamber forming layer 121, a distance between the heating elements 31 and the electrolyte body 2 is shortened. Accordingly, a period of time required to heat the electrolyte body 2 to its activation temperature can be shortened.

As a modification of this embodiment, the heating elements 31 may be buried within the heater substrate 32 in the same manner as in the first embodiment, or the sensing member 1C may have the measured gas chamber 124 and the spacer 123.

Embodiment 9

Another gas sensing member will be described with reference to FIGS. 26 to 28.

Figure 26:
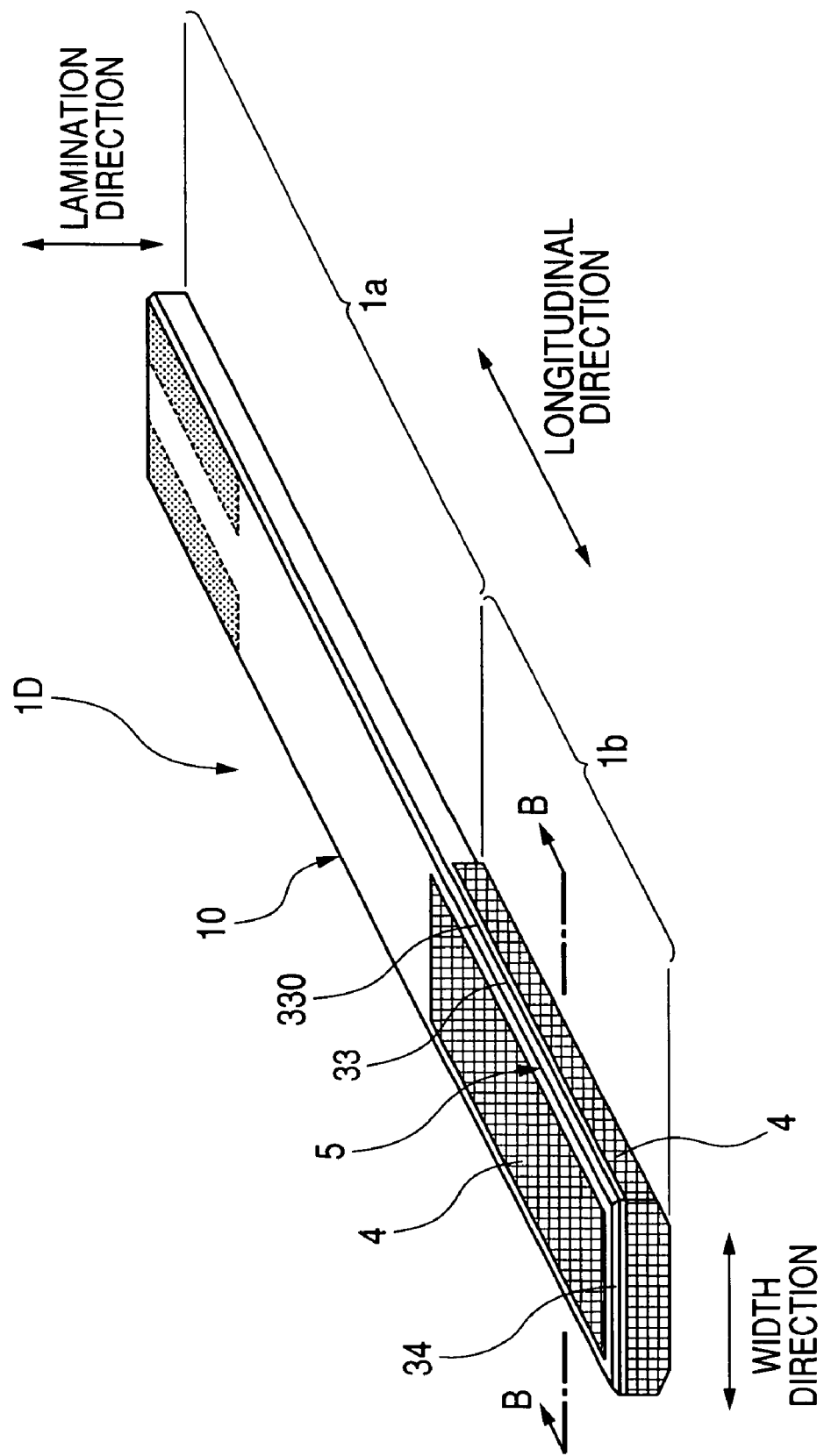
FIG. 26 is a perspective side view of a gas sensing member according to the ninth embodiment of the present invention.

FIG. 26 is a perspective side view of a gas sensing member according to the ninth embodiment of the present invention. FIG. 27 is a vertical sectional view taken substantially along line B-B of FIG. 26. FIG. 28 is a side view of the sensing member shown in FIG. 26. A plan view of the sensing member shown in FIG. 2 is shown in FIG. 4.

As shown in FIGS. 26 to 28 and FIG. 4, a gas sensing member 1D has the same unit structure 10 as that of the sensing member 1 shown in FIGS. 1 to 5. The sensing member 1D differs from the sensing member 1 in that a part of the bottom surface 320 of the heater substrate 32 is also covered with the porous protective layer 4, in addition to the coating surface area of the unit structure 10. That is, a second coating surface area covered with the protective layer 4 is placed on the bottom surface 320 of the heater substrate 32 except for parts of the bottom surface 320 adjacent to the side corner areas 33 and 330. Therefore, an uncovered surface area 5 is placed at the whole side corner areas 33 and 330 of the heater substrate 32, the whole front corner surface 34 of the heater substrate 32, parts of the bottom surface 320 of the heater substrate 32 adjacent to the side corner areas 33 and 330 and parts of the side surfaces 100 of the chamber forming layer 121 adjacent to the side corner areas 33 and 330.

More specifically, the ratio D1/D2 is set to be equal to or larger than 0.05, in the same manner as in the sensing member 1 shown in FIG. 2. Further, each side corner area 33 is spaced by a distance D3 along the width direction from a corresponding end of the protective layer 4 disposed on the bottom surface 320 (i.e., an end of the uncovered surface area 5 on the bottom surface 320). The bottom surface 320 has a width W1 along the width direction. A ratio D3/W1 of the distance D3 to the width W1 is set to be equal to or larger than 0.02 (D3/W1≧0.02).

The inventors have conducted experiments to examine a relation between the ratio D3/W1 and a percentage of generation of cracks in a gas sensing member. To conduct experiments, a gas sensing member wholly covered with the protective layer 4 (D3/W1=0) was prepared as a sample No. 1. Further, gas sensing members set at the ratios D3/W1=0.01, D3/W1=0.02, D3/W1=0.05 D3/W1=0.10, D3/W1=0.40, and D3/W1=0.70 are prepared as samples No. 2, No. 3, No. 4, No. 5, No. 6 and No. 7, respectively. The other conditions for the experiments are the same as those shown in Table 3. The ratio of crack generation is calculated in the same manner as that shown in Table 2. Examined results are indicated in Table 4.

TABLE 4

| Sample | D3/W1 | Percentage of Crack Generation (%) |
|---|---|---|
| No. 1 | 0 | 100 |
| No. 2 | 0.01 | 20 |
| No. 3 | 0.02 | 0 |
| No. 4 | 0.05 | 0 |
| No. 5 | 0.10 | 0 |
| No. 6 | 0.40 | 0 |
| No. 7 | 0.70 | 0 |

As shown in Table 4, in case of the ratio D3/W1 equal to or smaller than 0.01, cracks are generated in the unit structure 10. In contrast, in case of the ratio D3/W1 equal to or larger than 0.02, because water attached on the side corner area 33 is hardly held in the protective layer 4 disposed on the bottom surface 320 due to the Leidenfrost phenomenon, the temperature drop on the bottom surface 320 is reduced. Therefore, no cracks are generated in the sensing member.

Accordingly, when the protective layer 4 is disposed on the bottom surface 320 of the heater substance 32 so as to satisfy the ratio D3/W1 equal to or larger than 0.02, generation of cracks and breakages in the sensing member can be suppressed. Further, because the protective layer 4 is not disposed on the whole surface of the unit structure 10, a heat capacity of the sensing member can be reduced, so that the electrolyte body 2 can be quickly heightened to its activation temperature when the operation of the engine is started.

Next, a method of manufacturing the gas sensing member 1D shown in FIG. 26 to FIG. 28 will be described.

Figure 29:
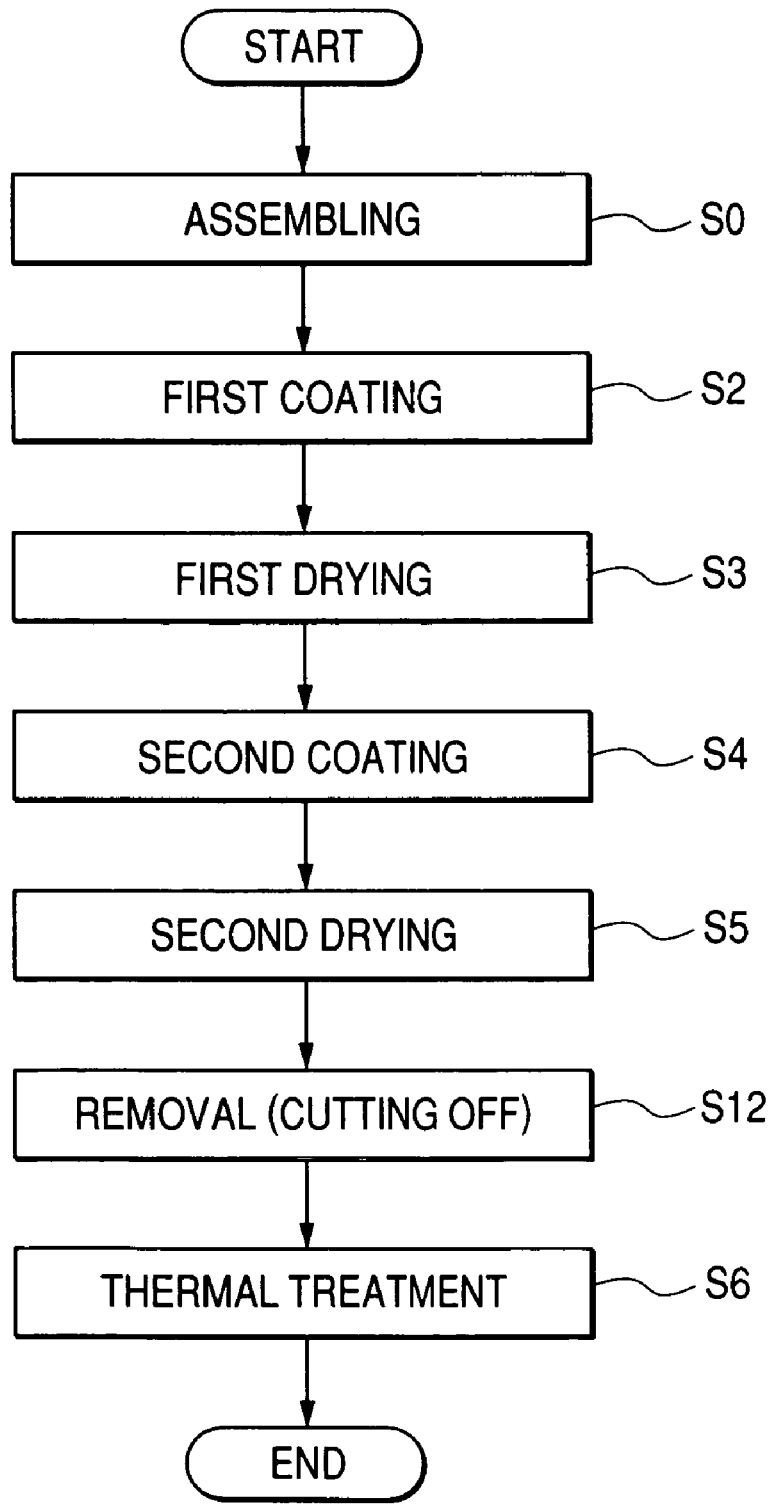
FIG. 29 is a flow chart showing a method of manufacturing the sensing member shown in FIG. 26 to FIG. 28 according to the ninth embodiment.
Figure 30:
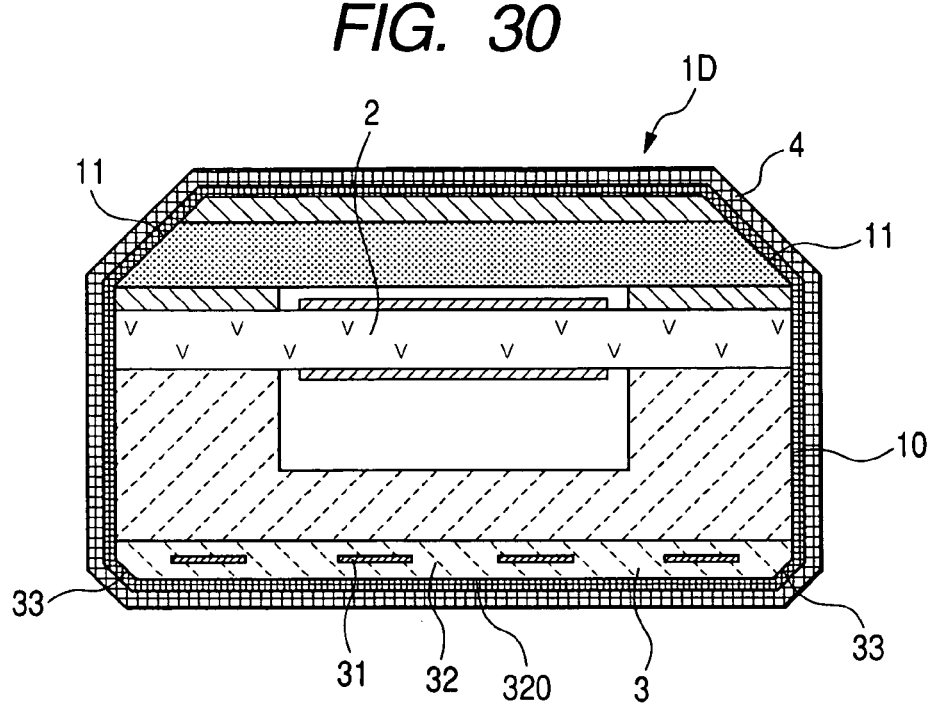
FIG. 30 is a vertical sectional view of a gas sensing member having a porous protective layer formed on the whole surface thereof.
Figure 31:
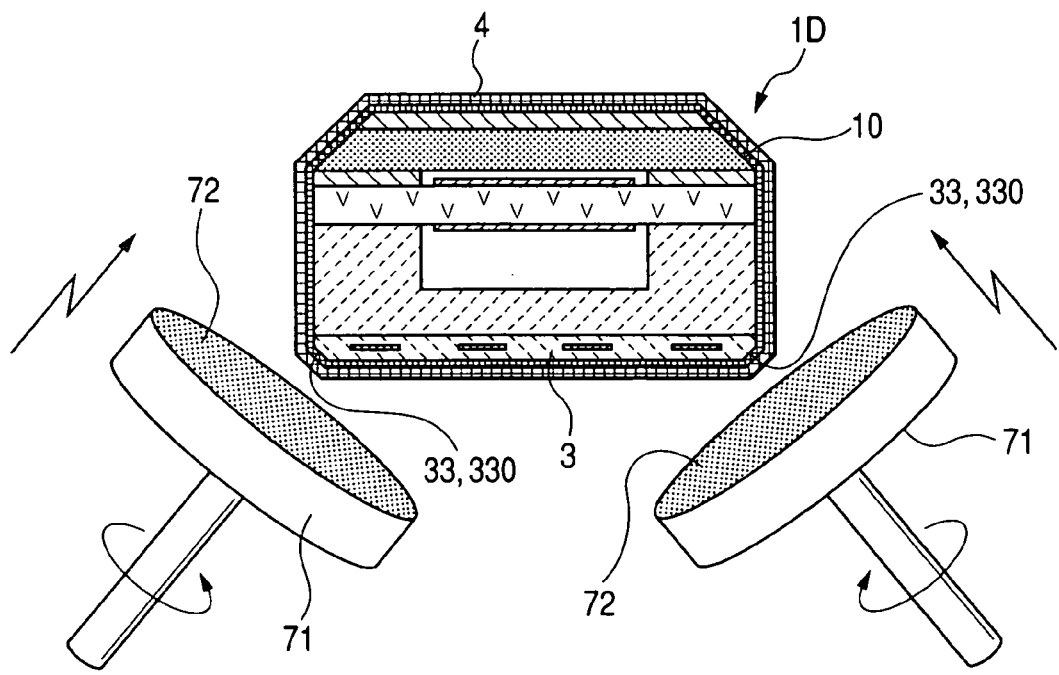
FIG. 31 is an explanatory view showing a step of cutting off portions of the protective layer from the sensing member shown in FIG. 30 by using a waterproof sandpaper.
Figure 32:
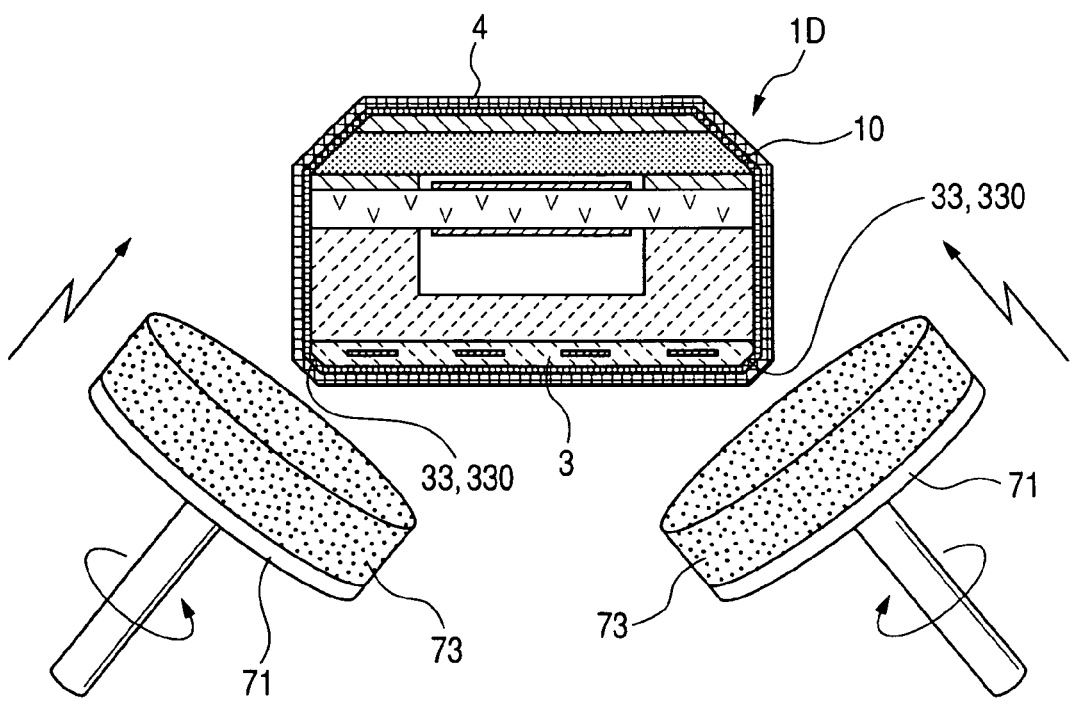
FIG. 32 is an explanatory view showing a step of cutting off portions of the protective layer from the sensing member shown in FIG. 30 by using an elastic grinding tool.
Figure 33:
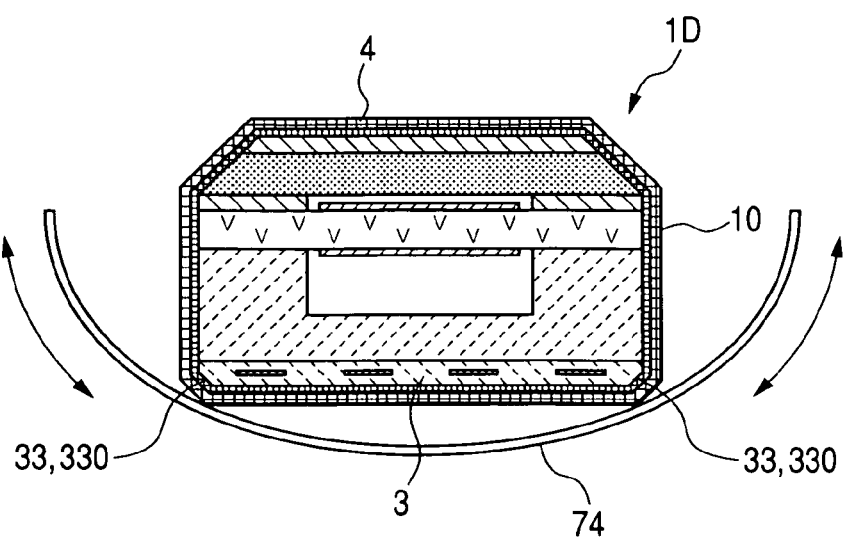
FIG. 33 is an explanatory view showing a step of cutting off portions of the protective layer from the sensing member shown in FIG. 30 by using a belt-like grinding device.

FIG. 29 is a flow chart showing a method of manufacturing the sensing member 1D according to the ninth embodiment. FIG. 30 is a vertical sectional view of a gas sensing member having a porous protective layer formed on the whole surface thereof. FIG. 31 is an explanatory view showing a step of cutting off portions of the protective layer from the sensing member shown in FIG. 30 by using a waterproof sandpaper. FIG. 32 is an explanatory view showing a step of cutting off portions of the protective layer from the sensing member shown in FIG. 30 by using an elastic grinding tool. FIG. 33 is an explanatory view showing a step of cutting off portions of the protective layer from the sensing member shown in FIG. 30 by using a belt-like grinding device.

In a method of manufacturing the sensing member 1D, the unit structure 10 is first assembled at step S0. Then, a third method of forming the protective layer 4 on coating surface areas of the unit structure 10 is performed. That is, as shown in FIG. 29, at the steps S2 and S4, the protective layer 4 not baked (i.e., protective layer forming material) is twice attached on the whole surface of the unit structure 10 of the portion 1b including the gas inlets 11, without attaching any mask layer on the unit structure 10. Therefore, the sensing member 1D shown in FIG. 30 is obtained. Then, the protective layer 4 not baked is dried at steps S3 and S5. Then, at step S12, portions of the protective layer 4 are removed from the sensing member 1D. Then, at step S6, a thermal treatment is performed for the protective layer 4 remaining in the sensing member 1D, in the same manner as the first method shown in FIG. 6. Therefore, as shown in FIG. 27, the sensing member 1D having the protective layer 4 on the coating surface area and the second coating surface area is obtained.

More specifically, as shown in FIG. 31, the protective layer 4 not baked is attached on the whole surface of the unit structure 10 and is dried at steps S2 to S5. Thereafter, at step S12, a waterproof sandpaper 72 is stuck on a grinding device 71, and the sandpaper 72 is pushed against the protective layer 4 disposed on the side corner areas 33 and 330 and areas near the areas 33 and 330 while rotating the grinding device 71, so that portions of the protective layer 4 are ground and cut off. To cut off portions of the protective layer 4 disposed on the bottom surface 320 and the side surface 100, an angle between the grinding device 71 and the sensing member 1D is adjusted. A sandpaper of No. #200 prescribed in JIS R6253 is, for example, used as the sandpaper 72. However, the number of the sandpaper can arbitrarily be selected.

Accordingly, because portions of the protective layer 4 are cut off after slurry dipping and drying according to the third method of forming the protective layer 4, the protective layer 4 disposed on the uncovered surface area 5 (see FIG. 27) can be reliably removed while considerably reducing the protective layer 4 remaining on the uncovered surface area 5, and durability of the sandpaper 72 can be enhanced. Further, workability in the cutting can be heightened, and productivity of the sensing member can be heightened.

In this embodiment, the protective layer 4 is cut off before the baking thereof. However, the protective layer 4 may be cut off after the baking of the protective layer 4.

Further, as shown in FIG. 32, the protective layer 4 not baked may be ground and cut off by using an elastic grinding tool 73 which is formed of elastic foam body such as foam rubber including abrasive grains. The grinding tool 73 is fixed on the grinding device 71 and is pushed against portions of the protective layer 4 while rotating the grinding device 71. Therefore, as shown in FIG. 27, portions of the protective layer 4 disposed on the uncovered surface area 5 are cut off.

The grinding tool 73 is, for example, obtained by coating specific sponge with abrasive grains of aluminium oxide. The grinding tool 73 is preferably superior in cutting performance and flexibility. The cutting performance can be adjusted by appropriately selecting size of abrasive grains and hardness of sponge material. For example, SF (No. #320 to No. #600) manufactured in Sumitomo Three M Co. LTD. is preferably used as the grinding tool 73.

Moreover, as shown in FIG. 33, the protective layer 4 not baked may be ground and cut off by using a belt-like grinding device 74 wherein abrasive grains are attached on a surface of a belt-like element. The belt-like grinding device 74 is pushed against the protective layer 4 such that the surface of the grinding device 74 is simultaneously in contact with the two side corner areas 33, and portions of the protective layer 4 disposed on the side corner areas 33 are simultaneously cut off.

Accordingly, because portions of the protective layer 4 disposed on the uncovered surface area 5 are ground and cut off, the uncovered surface area 5 not covered with the protective layer 4 can be easily and reliably obtained while at least the gas inlets 11 are covered with the protective layer 4.

Further, because the elastic grinding tool 73 is used to grind and cut off the protective layer 4, the grinding tool 73 can be easily deformed in conformity with the shape of the uncovered surface area 5. Accordingly, the protective layer 4 disposed on the surfaces of the unit structure 10 adjacent to the side corner areas 33 and 330 can efficiently be cut off, in addition to the protective layer 4 disposed on the side corner areas 33 and 330.

Moreover, the belt-like grinding device 74 used to grind and cut off the protective layer 4 can be arbitrarily curved. Therefore, One end portion of the grinding device 74 can be easily in contact with one side corner area 33 or 330 and surfaces of the unit structure 10 adjacent to one side corner area, while the other end portion of the grinding device 74 is simultaneously in contact with the other side corner area 33 or 330 and surfaces of the unit structure 10 adjacent to the other side corner area. Accordingly, the protective layer 4 disposed on the side corner areas 33 and 330, the surfaces of the unit structure 10 adjacent to the side corner areas 33 and 330 can efficiently be ground and cut off, and productivity of the sensing member 1D can be enhanced.

In this embodiment, the sensing member 1D is manufactured by cutting off the protective layer 4. However, the sensing member 1D may be manufactured according to the method shown in FIG. 6 by masking the uncovered surface area 5 with a mask layer, coating the inner and outer protective layer forming materials on the whole surface of the unit structure 10, drying the forming materials, baking the forming materials to form the protective layer 4, and removing the protective layer 4 formed on the uncovered surface area 5.

Embodiment 10

Figure 34:
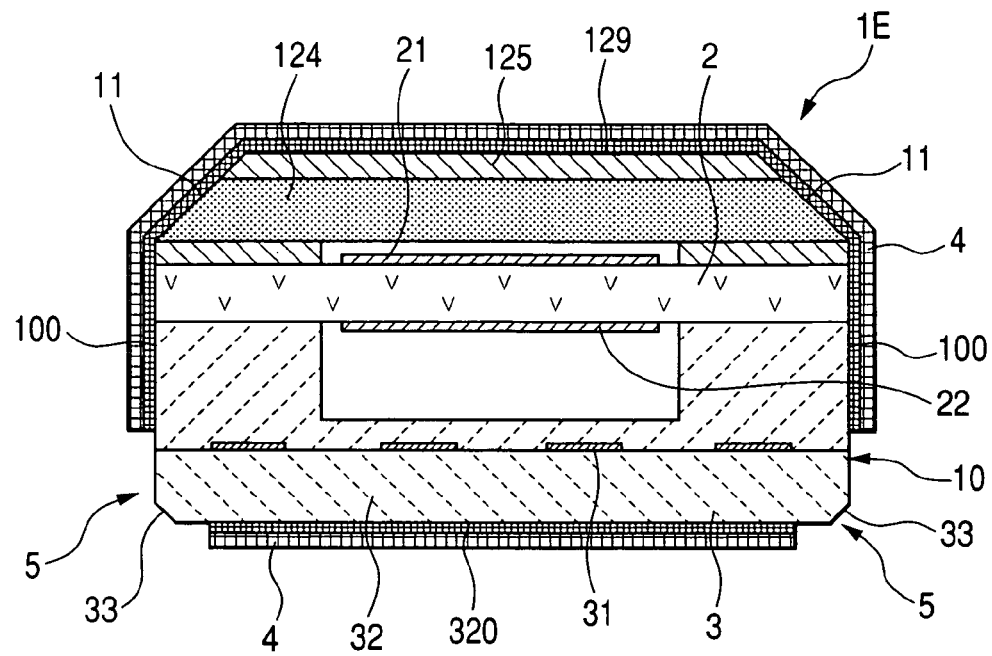
FIG. 34 is a vertical sectional view of a gas sensing member according to the tenth embodiment of the present invention.

FIG. 34 is a vertical sectional view of a gas sensing member according to the tenth embodiment of the present invention.

As shown in FIG. 34, a gas sensing member 1E has the protective layers 4 in the same manner as the sensing member 1D in the ninth embodiment. The sensing member 1E differs from the sensing member 1D in that the heating elements 31 are disposed on the heater substrate 32 so as to be directly in contact with the chamber forming layer 121.

Parts of the side surfaces 100 placed on both sides of the sensing member 1E in the width direction are heated to a high temperature by the heating elements 31, in the same manner as the side corner areas 33. Therefore, no protective layer 4 is disposed on the parts of the side surfaces 100 to prevent cracks or breakage of the sensing member 1D.

With this arrangement of the sensing member 1E, a distance between the heating elements 31 and the electrolyte body 2 is shortened, as compared with that in the sensing member 1D. Accordingly, a period of time required to heat the electrolyte body 2 to its activation temperature can be shortened.

Embodiment 11

In cases where a gas sensing member is figured so as to have an angular corner portion in the width direction, thermal stress is easily concentrated on the side corner portion. To prevent the generation of thermal stress, each of the sensing members 1 and 1D shown in FIGS. 2 and 27 is chamfered to remove four angular corner portions from the sensing member. However, a gas sensing member may have four angular corner portions.

Figure 35:
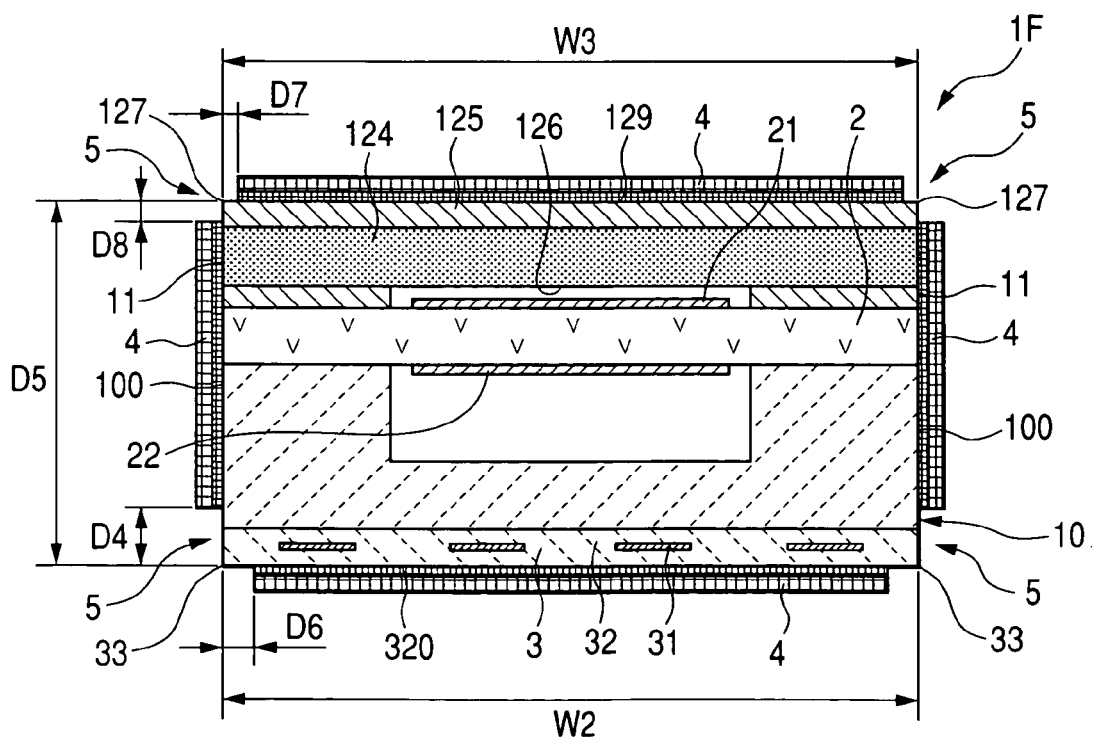
FIG. 35 is a vertical sectional view of a gas sensing member according to the eleventh embodiment of the present invention.

FIG. 35 is a vertical sectional view of a gas sensing member according to the eleventh embodiment of the present invention.

As shown in FIG. 35, a gas sensing member 1F differs from the sensing member 1D in the ninth embodiment in that the sensing member 1F has two angular corner portions of the heater 3 and two angular corner portions of the shielding layer 125 in the width direction such that the corner portions and surface areas of the unit structure 10 adjacent to the corner portions are not covered with the protective layer 4 so as to be directly exposed to the atmosphere or the measured gas.

More specifically, an uncovered surface area 5 is placed on upper corner portions 127 of the shielding layer 125, lower corner portions 33 of the heater substrate 32, parts of the top surface 129 near the upper corner portions 127, parts of the side surface 100 near the corner portions 33 and 127, and parts of the bottom surface 320 near the lower corner portions 33. At least the gas inlets 11 are covered with the protective layer 4.

Each lower corner portion 33 is spaced by a distance D4 along the lamination direction from a lower end of the protective layer 4 disposed on the side surface 100. Each lower corner portion 33 is spaced by a distance D5 (i.e., height of the side surface 100) along the lamination direction from the corresponding upper corner portion 127. The ratio D4/D5 is set to be equal to or larger than 0.2. The ratio D4/D5 is preferably set at 0.2. The ratio D4/D5 may be set to be equal to or larger than 0.05 (D4/D5$\geq$0.05), in the same manner as the ratio of D1/D2 in the member 1 shown in FIG. 2.

Each lower corner portion 33 is spaced by a distance D6 along the width direction from a corresponding side end of the protective layer 4 disposed on the bottom surface 320. The bottom surface 320 has a width W2 along the width direction. The ratio D6/W2 is set to be equal to or larger than 0.1. The ratio D6/W2 is preferably set at 0.1. The ratio D6/W2 may be set to be equal to or larger than 0.02 (D6/W2$\geq$0.02), in the same manner as the ratio of D3/W1 in the member 1D shown in FIG. 27.

Each upper corner portion 127 is spaced by a distance D7 along the width direction from a corresponding side end of the protective layer 4 disposed on the top surface 129. The top surface 129 has a width W3 along the width direction. The ratio D7/W3 is set to be equal to or larger than 0.05. The ratio D7/W3 is preferably set at 0.05.

Each upper corner portion 127 is spaced by a distance D8 along the lamination direction from an upper end of the protective layer 4 disposed on the side surface 100. The ratio D8/D5 is set to be equal to or larger than 0.1. The ratio D8/D5 is preferably set at 0.1.

With this arrangement of the sensing member 1F, even when water is attached on the corner portion 33 or 127, a temperature drop of the corner portion becomes small due to the Leidenfrost phenomenon. Further, even when water attached on the protective layer 4 reaches the outer surface of the shielding layer 125 or the heater substrate 32, the water does not reach any corner portion.

Figure 27:
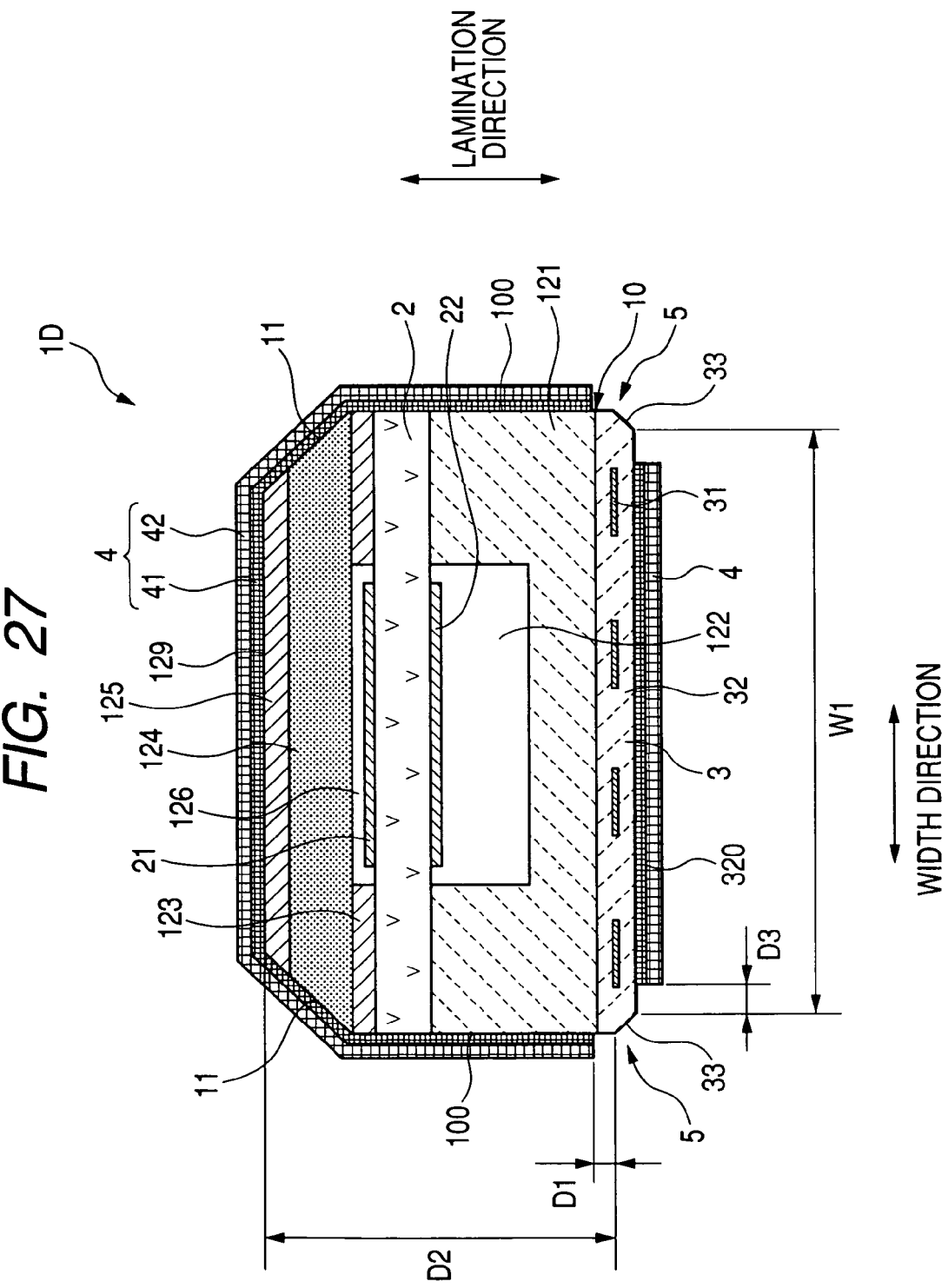
FIG. 27 is a vertical sectional view taken substantially along line B-B of FIG. 26.
Figure 28:
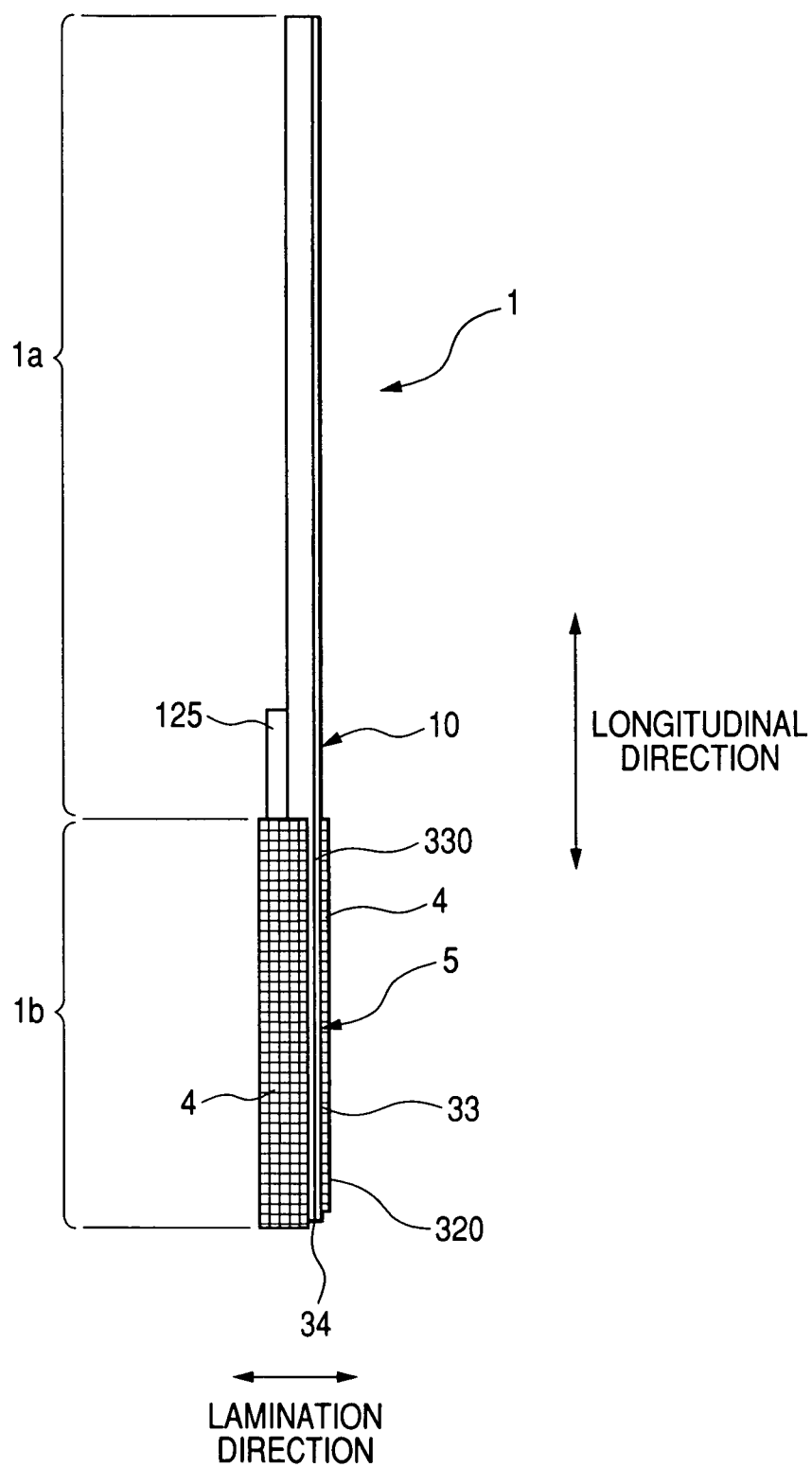
FIG. 28 is a side view of the sensing member shown in FIG. 26.

Accordingly, cracks or breakages of the sensing member 1F can be reduced, in the same manner as in the sensing member 1D shown in FIG. 27.

Embodiment 12

Figure 36:
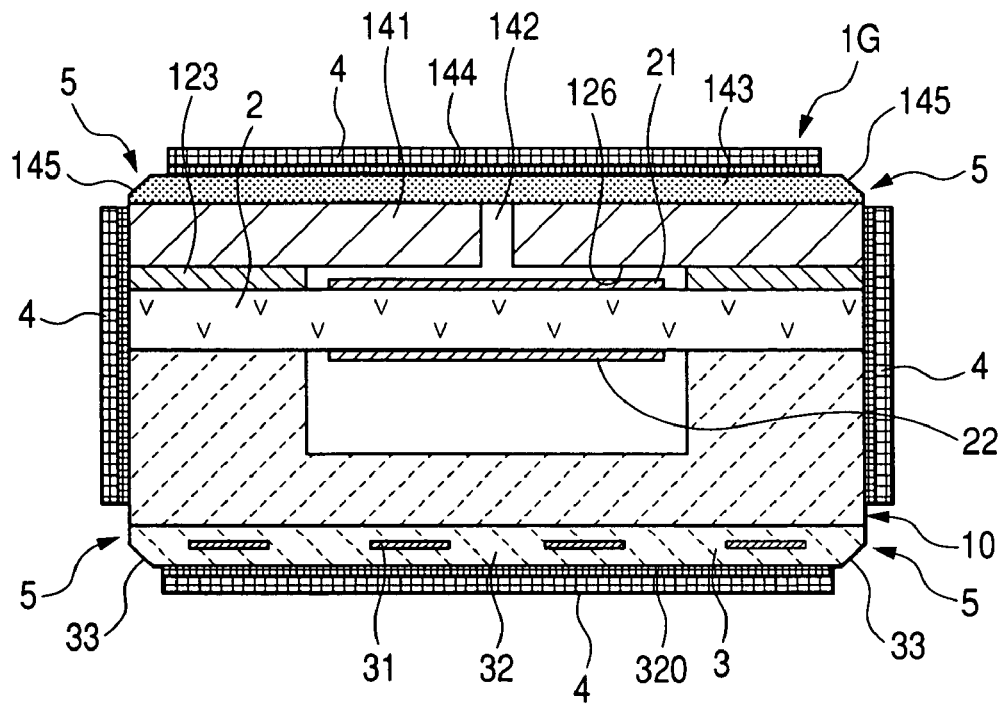
FIG. 36 is a vertical sectional view of a gas sensing member according to the twelfth embodiment of the present invention.

FIG. 36 is a vertical sectional view of a gas sensing member according to the twelfth embodiment of the present invention.

As shown in FIG. 36, a gas sensing member 1G differs from the sensing member 1D in the ninth embodiment in that the sensing member 1G has a dense layer 141 disposed on the spacer 123 and a porous layer 143 disposed on the dense layer 141. The measured gas is transmittable through the porous layer 143 but is impossible to be transmitted through the dense layer 141. The dense layer 141 has at least one pin hole 142. The measured gas passing through the porous layer 143 enters at the pin hole 142 and reaches the gas chamber 126. Therefore, the pin hole 142 acts as a gas inlet. The porous layer 143 is chamfered to remove its corner portions in the width direction, so that upper side corner areas 145 are, respectively, formed on the chamfered surfaces of the porous layer 143.

An uncovered surface area 5 is placed on the upper side corner areas 145 and surface areas near the areas 145, in addition to the side corner areas 33, surface areas near the areas 33 and the whole front surface 34 (see FIG. 26).

With this arrangement of the sensing member 1G, a measured gas passes through the protective layer 4 disposed on a top surface 144 of the porous layer 143 and the porous layer 143. Then, the measured gas enters at the pin hole 142 and reaches the gas chamber 126. Therefore, a flow rate of the measured gas reaching the gas chamber 126 is determined by a size of the pin hole 142 and the number of pin holes.

Accordingly, because the side corner areas 145 of the porous layer 143 are formed by chamfering the porous layer 143 and are exposed to the atmosphere or the measured gas, cracks or breakages of the sensing member 1G can be reduced, in the same manner as in the sensing member 1D shown in FIG. 27.

Embodiment 13

Figure 37:
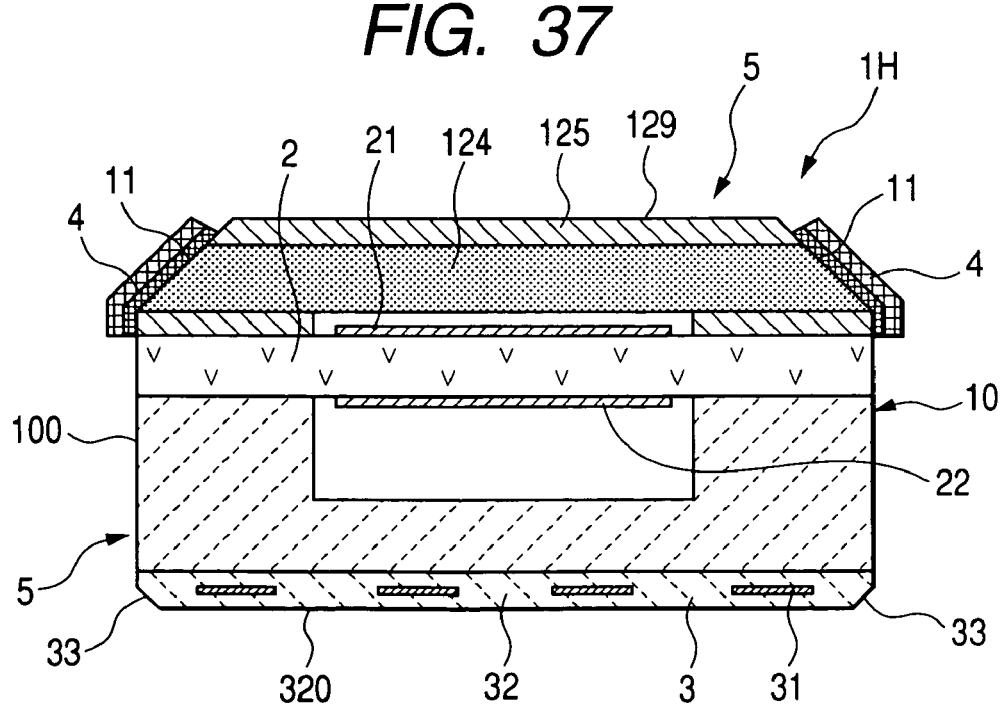
FIG. 37 is a vertical sectional view of a gas sensing member according to the thirteenth embodiment of the present invention.

FIG. 37 is a vertical sectional view of a gas sensing member according to the thirteenth embodiment of the present invention.

As shown in FIG. 37, a gas sensing member 1H has the same unit structure 10 as that of the sensing member 1 in the first embodiment. The sensing member 1H differs from the sensing member 1 in that the protective layer 4 is disposed only on the gas inlets 11 (i.e., the side surfaces of the porous diffused resistor layer 124 in the width direction). The protective layer 4 may additionally be disposed on surface areas of the unit structure 10 surrounding the gas inlets 11. An uncovered surface area 5 not covered with the protective layer 4 is placed on the whole top surface 129 of the unit structure 10 placed opposite to the heater 3 through the electrolyte body 2 along the lamination direction and the greater part of the side surfaces 100, in addition to the whole surface of the heater substrate 32 including the side corner areas 33 and 330.

With this arrangement of the sensing member 1H, the protective layer 4 having a minimum area required to trap poisons of the measured gas is disposed on the unit structure 10.

Because the shielding layer 125 is placed to be furthest away from the heating elements 31, the temperature of the top surface 129 is lower than the surface of the heater 3. Therefore, the generation of cracks or breakages caused by water attached on the top surface 129 can be suppressed in the sensing member regardless of whether the protective layer 4 is disposed on the top surface 129. However, when no protective layer 4 is disposed on the top surface 129, the generation of cracks or breakages in the sensing member can further be suppressed, and a heat capacity of the sensing member can be reduced at the maximum.

Accordingly, the generation of cracks and breakages can further be suppressed in the sensing member. Further, a heat capacity of a gas sensing member can be minimized, and the electrolyte body 2 can further quickly be heightened to its activation temperature.

Embodiment 14

Figure 38:
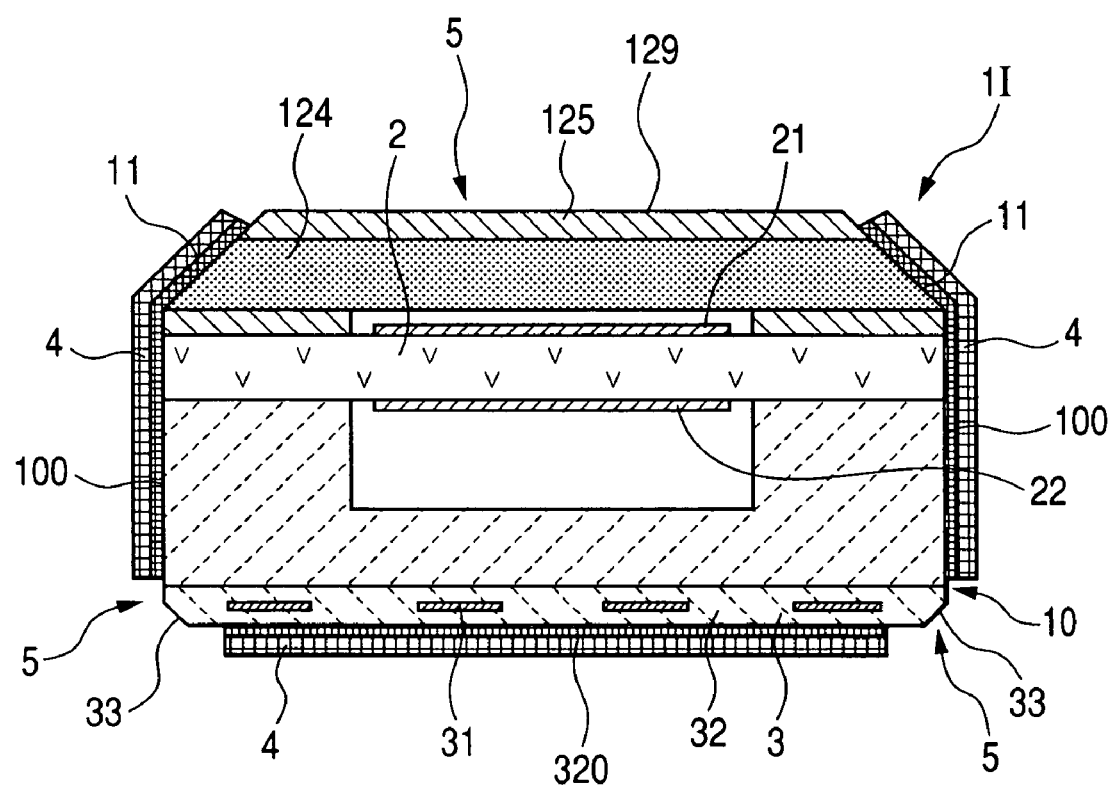
FIG. 38 is a vertical sectional view of a gas sensing member according to the fourteenth embodiment of the present invention.

FIG. 38 is a vertical sectional view of a gas sensing member according to the fourteenth embodiment of the present invention.

As shown in FIG. 38, a gas sensing member 1I has the same unit structure 10 as that of the sensing member 1D in the ninth embodiment. The sensing member 1H differs from the sensing member 1D in that the protective layer 4 is not disposed on the top surface 129 of the unit structure 10 so as to directly expose the top surface 129 to the atmosphere or the measured gas. An uncovered surface area 5 not covered with the protective layer 4 is placed on the whole top surface 129 of the unit structure 10 placed opposite to the heater 3 through the electrolyte body 2 along the lamination direction, in addition to the whole side corner areas 33 and 330 and surface areas near the side corner areas 33 and 330.

With this arrangement of the sensing member 1I, as compared with the sensing member 1D, the generation of cracks or breakages caused by water attached on the top surface 129 can further be suppressed in the sensing member 1I, and a heat capacity of the sensing member 1I can be reduced.

In these embodiments, the protective layer 4 of the sensing member 1 shown in FIG. 1 to FIG. 5 may be formed on the unit structure 10 according to the third method shown in FIG. 29 by cutting off the protective layer 4 without masking the uncovered surface area 5 with a mask layer.

Further, the protective layer 4 of each of the sensing members 1E to 1I shown in FIG. 34 to FIG. 38 may be formed on the unit structure 10 according to any of the first method shown in FIG. 6, the second method shown in FIG. 18 and the third method shown in FIG. 29.

What is claimed is:

1. A gas sensing member to be exposed to a measured gas, comprising:

A unit structure having a first surface area and a second surface area and having a gas inlet, at which the measured gas enters, on the first surface area; and A porous protective layer, which removes poison from the measured gas before the measured gas enters at the gas inlet of the unit structure, disposed on the first surface area of the unit structure, The unit structure comprising:

A solid electrolyte body, through which oxygen ions are transmittable, which has both surfaces opposite to each other along a lamination direction;

A porous diffused resistor layer through which the measured gas entering at the gas inlet is transmitted;

A gas measurement electrode which is disposed on one surface of the solid electrolyte body and is exposed to the measured gas after the measured gas enters at the gas inlet and is transmitted through the porous diffused resistor layer;

A reference gas electrode which is disposed on the other surface of the solid electrolyte body and is exposed to a reference gas;

A heater which is disposed on or close to the solid electrolyte body so as to face one of the surfaces of the solid electrolyte body and has a heater substrate and a heating element disposed in or on the heater substrate, the heating element heating the solid electrolyte body;

A chamber forming layer disposed between the solid electrolyte body and the heater so as to form a reference gas chamber between the solid electrolyte body and the chamber forming layer, and Wherein the heater substrate of the heater has a side corner area which is disposed at a side corner of the unit structure in a width direction of the unit structure, the width direction being substantially perpendicular to the lamination direction, and the side corner area extends along a longitudinal direction of the unit structure, the longitudinal direction being substantially perpendicular to both the lamination and width directions, so as to be adjacent to the heating element along the width direction, Wherein the porous protective layer is not disposed on the second surface area of the unit structure, and at least a portion of the side corner area of the heater substrate is disposed in the second surface area of the unit structure, Wherein a first distance D1 along the lamination direction from the side corner area of the heater substrate to the porous protective layer and a second distance D2 along the lamination direction from the side corner area of the heater substrate to a surface of the unit structure opposite to the heater with respect to the solid electrolyte body are set to satisfy a relation of D1/D2 equal to or larger than 0.05 and equal to or smaller than 0.7, Wherein the porous protective layer is disposed on at least a portion of the chamber forming layer, and Wherein the side corner area is chamfered.

2. The gas sensing member according to claim 1, wherein the entire side corner area of the heater substrate is disposed in the second surface area of the unit structure.

3. The gas sensing member according to claim 1, wherein the heater substrate has a second side corner area which is disposed at the side corner of the unit structure and extends from the side corner area along the longitudinal direction so as to be adjacent to no heating element along the width direction, and the unit structure is covered with the porous protective layer such that 60% or more of a combined area of the side corner area and the second side corner area is disposed in the second surface area of the unit structure.

4. The gas sensing member according to claim 1, wherein the heater substrate has a front surface which is placed on a front corner of the unit structure in the longitudinal direction and extends along the width direction so as to be adjacent to the heating element along the longitudinal direction, and at least a part of the front surface of the heater substrate is disposed in the second surface area of the unit structure.

5. The gas sensing member according to claim 1, wherein the heater substrate has a bottom surface which is placed on a bottom side of the unit structure in the lamination direction, and a part of the bottom surface of the heater substrate is disposed in the first surface area of the unit structure such that a distance D3 along the width direction from the side corner area of the heater substrate to the part of the bottom surface and a width W1 of the bottom surface along the width direction are set to satisfy a relation of D3/W1 equal to or larger than 0.02 and smaller than 0.5.

6. The gas sensing member according to claim 1, wherein the porous protective layer is made of γ-alumina, θ-alumina or titania as a major component.

7. The gas sensing member according to claim 1, wherein the porous protective layer has a plurality of layer portions respectively formed of particles such that, as the layer portion becomes far from the first surface area of the unit structure, a size of the particles of the layer portion becomes large.

8. The gas sensing member according to claim 7, wherein the porous protective layer has a first layer portion disposed on the first surface area of the unit structure and a second layer portion disposed on the first layer portion, an average size of the particles of the first layer portion is set within a range from 1 to 40 µm, and an average size of the particles of the second layer portion is set within a range from 2 to 100 µm.

9. The gas sensing member according to claim 1, wherein the porous protective layer includes a catalyst made of a metal or a metallic oxide.

10. The gas sensing member according to claim 9, wherein the catalyst contains at least platinum, rhodium, ruthenium, or palladium as the metal.

11. The gas sensing member according to claim 9, wherein the catalyst is made of a noble metal having an average size of particles set within a range from 0.01 to 5 µm.

12. The gas sensing member according to claim 9, wherein the catalyst is made of a noble metal having an average size of particles set within a range from 0.1 to 2 µm.

13. The gas sensing member according to claim 9, wherein the catalyst contains titania as the metallic oxide.

14. The gas sensing member according to claim 9, wherein a content of the catalyst is set to be 10 µg/cm$^2$ or more per unit area of a projected area which is defined on a plane perpendicular to a gas passing direction of the measured gas passing through the porous protective layer.

15. The gas sensing member according to claim 9, wherein a content of the catalyst is set within a range from 10 to 500 µg/cm$^2$ per unit area of a projected area which is defined on a plane perpendicular to a gas passing direction of the measured gas passing through the porous protective layer.

16. The gas sensing member according to claim 1, wherein the poison removed by the porous protective layer comprises components not yet burned in the measured gas.

17. The gas sensing member according to claim 1, wherein the unit structure has a shielding layer disposed on the porous diffused resistor layer so as to place at least a portion of the shielding layer between the porous diffused resistor layer and the porous protective layer.

18. The gas sensing member according to claim 1, wherein there are two chamfered side corner areas, one disposed at each side corner of the unit structure, adjacent the heating element and extending along the longitudinal direction.

19. The gas sensing member according to claim 18, wherein the heater substrate further has two second side corner areas each disposed at a respective side corner of the unit structure in the width direction and extending from said side corner areas adjacent to the heating element, away from the heating element, along the longitudinal direction, so as to be adjacent to no heating element along the width direction, and the unit structure is covered with the porous protective layers such that 60% or more of a confined area of the side corner areas and the second side corner areas is disposed in the second surface area of the unit structure.

* * * * *